(12) United States Patent
Lin

(10) Patent No.: US 9,249,183 B2
(45) Date of Patent: Feb. 2, 2016

(54) MODULATORS FOR SIRT6 AND ASSAYS FOR SCREENING SAME

(75) Inventor: Hening Lin, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 13/996,297

(22) PCT Filed: Dec. 21, 2011

(86) PCT No.: PCT/US2011/066480
§ 371 (c)(1),
(2), (4) Date: Sep. 11, 2013

(87) PCT Pub. No.: WO2012/088268
PCT Pub. Date: Jun. 28, 2012

(65) Prior Publication Data
US 2013/0345155 A1    Dec. 26, 2013

Related U.S. Application Data

(60) Provisional application No. 61/426,231, filed on Dec. 22, 2010.

(51) Int. Cl.
*C07C 327/42* (2006.01)
*C07K 7/06* (2006.01)
*C07K 5/11* (2006.01)
*C12Q 1/34* (2006.01)

(52) U.S. Cl.
CPC ............ *C07K 5/1019* (2013.01); *C07C 327/42* (2013.01); *C07K 7/06* (2013.01); *C12Q 1/34* (2013.01); *G01N 2333/98* (2013.01)

(58) Field of Classification Search
None
See application file for complete search history.

(56) References Cited

U.S. PATENT DOCUMENTS

| | | |
|---|---|---|
| 6,552,225 B1 | 4/2003 | Butlin et al. |
| 2005/0204410 A1 | 9/2005 | Karow et al. |
| 2006/0264415 A1 | 11/2006 | Leit de Moradei et al. |
| 2008/0305496 A1 | 12/2008 | Marmorstein et al. |
| 2010/0184869 A1 | 7/2010 | Bogo et al. |
| 2013/0023528 A1 | 1/2013 | Ratan et al. |

FOREIGN PATENT DOCUMENTS

| | | |
|---|---|---|
| DE | 32 04 735 A1 | 8/1983 |
| JP | 2000-212180 | 8/2000 |
| JP | 2009-161478 | 7/2009 |
| WO | WO 98/46559 A1 | 10/1998 |
| WO | WO 2009/049018 * | 4/2009 |
| WO | WO 2011/081945 A2 | 7/2011 |
| WO | WO 2012/006391 A2 | 1/2012 |

OTHER PUBLICATIONS

Suzuki et al., Bioorganic & Medicinal Chemistry Letters, 2009, 19, 5670-5672.*
Chinese Office Action dated Oct. 30, 2014 received from Application No. 201180068116.3, together with an English language translation.
Böttcher-Friebertshäuser et al., "Cleavage of Influenza Virus Hemagglutinin by Airway Proteases TMPRSS2 and HAT Differs in Subcellular Localization and Susceptibility to Protease Inhibitors", *Journal of Virology* 84(11):5605-5614 (Jun. 2010).
Dávalos A. et al., "miR-33a/b Contribute to the Regulation of Fatty Acid Metabolism and Insulin Signaling", *PNAS* 108(22):9232-9237 (May 31, 2011).
Du J. et al., "Sirt5 is a NAD-Dependent Protein Lysine Demalonylase and Desuccinylase", *Science* 334:806-809 (Nov. 11, 2011).
Huhtiniemi T. et al., "N-Modified Lysine Containing Inhibitors for SIRT1 and SIRT2", *Bioorganic & Medicinal Chemistry* 18:5616-5625 (2010).
Zhu A.Y. et al., "Plasmodium Falciparum Sir2A Preferentially Hydrolyzes Medium and Long Chain Fatty Acyl Lysine", *American Chemical Society* 7(1):155-159 (Oct. 12, 2011).
International Search Report dated Aug. 31, 2012 received from Application No. PCT/US2011/066480.

* cited by examiner

*Primary Examiner* — Karlheinz R Skowronek
*Assistant Examiner* — Roy Teller
(74) *Attorney, Agent, or Firm* — Scully, Scott, Murphy & Presser, P.C.

(57) ABSTRACT

Method for identifying a modulator of Sirt6, PfSir2a, or Sirt7 deacylase activity, wherein a fatty-acylated substrate containing an acyl-lysine moiety and an indicator moiety is contacted with Sirt6, PfSir2a, or Sirt7 in the presence of a candidate compound under conditions for Sirt6, PfSir2a, or Sirt7 to deacylate the substrate, wherein the acyl is a hydrophobic fatty acyl group containing a hydrocarbon group having at least three carbon atoms connected by carbon-carbon bonds; contacting the deacylated substrate with a cleavage agent that cleaves the linkage between the lysine and indicator moiety to generate a detectable signal; and correlating a quantified Sirt6, PfSir2a, or Sirt7 deacylase activity therefrom. Modulating compounds of Sirt6, PfSir2a, or Sirt7 deacylase activity are also described, as are pharmaceutical compositions thereof, methods of treatment by administration of the modulating compounds, and kits for practicing the method.

21 Claims, 7 Drawing Sheets

(A)

(B)

(A)

(B)

MODULATORS FOR SIRT6 AND ASSAYS FOR SCREENING SAME

CROSS-REFERENCE TO RELATED APPLICATIONS

This application claims priority from U.S. Provisional Application No. 61/426,231, filed Dec. 22, 2010, which is herein incorporated by reference in its entirety.

STATEMENT REGARDING FEDERALLY SPONSORED RESEARCH

This invention was made with government support under Contract No. GM086703 awarded by the National Institutes of Health. The government has certain rights in the invention.

BACKGROUND OF THE DISCLOSURE

Sirtuins are a class of enzymes known as nicotinamide adenine dinucleotide (NAD)-dependent deacetylases. Humans have seven sirtuins, Sirt1-7, that regulate a variety of biological processes, including aging, transcription, and metabolism. Therefore, small molecules that can regulate sirtuin activity can be used to treat several human diseases.

Of the seven human sirtuins, Sirt6 is of particular importance because of its roles in controlling metabolism and genome stability. The biological function of Sirt6 makes it a promising target to treat fatty liver diseases, obesity, and diabetes. Therefore, small molecules that can activate, inhibit, or otherwise modulate Sirt6 would be highly beneficial in treating such diseases and conditions.

The malaria parasite *Plasmodium falciparum* contains two sirtuins, PfSir2a and PfSir2b. These sirtuins are known to regulate the expression of virulence genes, antigenic variation, and antigenic gene expression, which helps the malaria parasite evade detection by the host's immune system. Thus, small molecules that can inhibit or otherwise beneficially modulate these sirtuins can be used in the treatment of malaria, which would also be highly beneficial.

The development of Sirt6 and PfSir2a inhibitors has been hampered by the lack of an effective activity assay for Sirt6 and PfSir2a, particularly one that can be used in a high-throughput manner. This difficulty in developing an effective activity assay for Sirt6 and PfSir2a is primarily a result of the very weak deacetylase activity of Sirt6 and PfSir2a. Among the seven mammalian sirtuins, Sirtuins 4-7 have either weak or no deacetylase activity. Sirt6 is known to function as a histone H3K9- and H3K56-specific deacetylase because other acetyl peptides cannot be hydrolyzed by Sirt6. However, the deacetylase activity is very weak and no $k_{cat}$ and $K_m$ measurement has thus far been reported. Similarly, the deacetylase activity of PfSir2a is known to be much weaker than that of human Sirt1.

BRIEF SUMMARY OF THE DISCLOSURE

It has been discovered herein that Sirt6 is a selective deacylase enzyme of acyl-lysine residues when the acyl group on the lysine is substantially hydrophobic, particularly when the acyl group contains a high carbon number (e.g., at least 5, 6, 7, 8, 9, 10, or greater carbon number) hydrocarbon group, such as a long-chain alkyl or alkenyl group. This selective activity of Sirt6 contrasts sharply with the known selectivities of other sirtuins. For example, Sirtuins 1, 2, and 3 have been known to have robust deacetylase activity, while Sirtuin 5 has been known to favorably remove malonyl, succinyl, and glutaryl groups from lysine residues. In contrast, it has been herein discovered that Sirt6 can remove long-chain hydrophobic fatty acyl groups from lysine residues significantly more effectively (e.g., more than 30-fold more effectively) than its deacetylase activity. Similar to Sirt6, the deacetylase activities of PfSir2a and Sirt7 have also been found to be very weak, while their ability to remove long chain fatty acyl groups has been found to be much more efficient.

Using this new found activity of Sirt6, a method is herein described in which the activity level of Sirt6 (and sirtuins having similar activity, such as PfSir2a and Sirt7) can be effectively determined under various conditions and in the presence of any of a number of possible Sirt6-modulating species. Thus, while observation of deacetylase activity is nearly ineffective for the purpose of determining an activity level or identifying modulators (i.e., regulators, including activators or inhibitors) of Sirt6, PfSir2a, or Sirt7, the instant invention has found a way to effectively determine an activity level or identify modulators of Sirt6, PfSir2a, or Sirt7 by employing a substrate containing a long-chain fatty acyl lysine structure and determining the efficiency of the Sirt6-, PfSir2a-, or Sirt7-mediated acyl hydrolysis under various conditions. The methodology described herein can also advantageously be practiced as a high-throughput screening for small molecules that can regulate Sirt6, PfSir2a, or Sirt7 activity.

The Sirt6-, PfSir2a-, or Sirt7-specific modulators identified by the methods described herein can be used in the treatment or prevention of various disorders characterized by an abnormal or non-optimal Sirt6, PfSir2a, or Sirt7 activity. These disorders include those related to metabolism (e.g., obesity), diabetes, malaria, and genome stability.

It has also been found herein that mammalian histones have long chain fatty acyl lysine modifications, and that Sirt6's physiological role is likely to remove these fatty acyl modifications. Thus, it appears that Sirt6 can control the transcription of certain genes by removing modifications on histones, which suggests that histone lysine long chain fatty acylation is a novel epigenetic modification involved in regulating transcription. Although it is well known that short fatty acyl modifications, such as acetylation, can regulate transcription, long chain fatty acylation, such as myristoylation on histones, has not been known, until now, to be involved in epigenetic modifications. Because transcription regulation is important for normal and diseased cells, the new epigenetic modification can be targeted to treat a number of disorders.

More specifically, the method (i.e., assay) for identifying a modulator of Sirt6, PfSir2a, or Sirt7 deacylase activity includes: (i) contacting an acylated substrate with Sirt6, PfSir2a, or Sirt7 in the presence of a candidate compound under conditions for Sirt6, PfSir2a, or Sirt7 to deacylate the substrate to provide a deacylated substrate, wherein the acylated substrate contains an acyl-lysine moiety and an indicator moiety, and the acyl contains a hydrocarbon group having at least three, four, or five carbon atoms connected by carbon-carbon bonds, wherein the hydrocarbon group optionally includes one heteroatom selected from O, N, and S that interrupts a carbon-carbon bond of the hydrocarbon group or replaces a carbon atom of the hydrocarbon group, except that the heteroatom is not included as an OH, SH, or $NH_2$ group, and wherein one or more hydrogen atoms in the hydrocarbon group is optionally replaced with fluoro atoms, and wherein the lysine may be derivatized in its side-chain E-aminobutyl group; (ii) contacting the deacylated substrate with a cleavage agent that cleaves the linkage between the lysine and indicator moiety to release the indicator moiety and generate a detectable signal having a signal intensity; and (iii) correlating the signal intensity with Sirt6, PfSir2a, or Sirt7 deacylase activity; wherein a change in Sirt6, PfSir2a, or Sirt7 deacylase activity in the presence of the candidate compound, relative to Sirt6, PfSir2a, or Sirt7 deacylase activity in the absence of the candidate compound, identifies the candidate compound as a modulator of Sirt6, PfSir2a, or Sirt7 deacylase activity.

The candidate compound can be any chemical species (e.g., molecule or macromolecule, such as a protein or nucleic acid) tested in the assay described above. Depending on the results of the assay, the candidate compound can be found to be a modulator (e.g., inhibitor or activator) or a non-modulator of Sirt6, PfSir2a, or Sirt7 deacylase activity. In particular embodiments, the candidate compound or modulator has the following chemical structure:

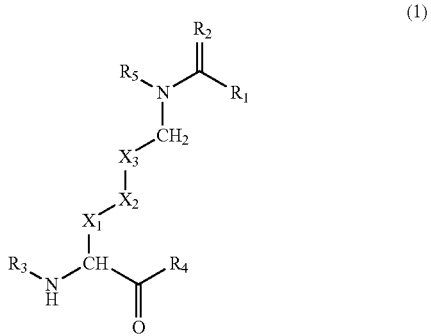
(1)

In Formula (1) above, $R_1$ is a hydrocarbon group having at least three, four, five, six, seven, eight, nine, or ten carbon atoms connected by carbon-carbon bonds, wherein the hydrocarbon group optionally includes one heteroatom selected from O, N, and S that interrupts a carbon-carbon bond of the hydrocarbon group or replaces a carbon atom of the hydrocarbon group, except that the heteroatom is not included as an OH, SH, or $NH_2$ group, and wherein one or more hydrogen atoms in the hydrocarbon group is optionally replaced with fluoro atoms; $R_2$ is selected from S, $NR_6$, and O, wherein $R_6$ is a hydrogen atom or a hydrocarbon group R; $X_1$, $X_2$, and $X_3$ are independently selected from —$(CH_2)_n$—, —$NR_{12}$—, —O—, —S—, or a bond, wherein $R_{12}$ is a hydrogen atom or a hydrocarbon group R, and wherein n represents 1, 2, or 3; $R_5$ is a hydrogen atom or a hydrocarbon group R; and $R_3$ and $R_4$ are independently hydrogen atom or a hydrocarbon group R; wherein the hydrocarbon groups R are independently either unsubstituted or substituted with one or more heteroatoms selected from N, O, S, P, and F or heteroatom groups containing one or more of the heteroatoms, wherein $R_4$ can alternatively be OH or SH.

The acylated substrate used in the assay described above has the features generally provided above in Formula (1) above, except that it must also contain an indicator moiety. In particular embodiments, the acylated substrate has the following chemical structure:

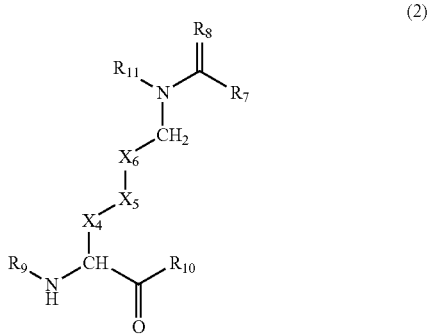
(2)

In Formula (2) above, $R_7$ is a hydrocarbon group having at least three, four, five, six, seven, eight, nine, or ten carbon atoms connected by carbon-carbon bonds, wherein the hydrocarbon group optionally includes one heteroatom selected from O, N, and S that interrupts a carbon-carbon bond of the hydrocarbon group or replaces a carbon atom of the hydrocarbon group, except that the heteroatom is not included as an OH, SH, or $NH_2$ group, and wherein one or more hydrogen atoms in the hydrocarbon group is optionally replaced with fluoro atoms; $R_8$ is selected from S, $NR_{13}$, and O, wherein $R_{13}$ is a hydrogen atom or a hydrocarbon group R; $X_4$, $X_5$, and $X_6$ are independently selected from —$(CH_2)_n$—, —$NR_{14}$—, —O—, —S—, or a bond, wherein $R_{14}$ is a hydrogen atom or a hydrocarbon group R, and wherein n represents 1, 2, or 3; $R_{11}$ is a hydrogen atom or a hydrocarbon group R; and $R_9$ and $R_{10}$ are independently hydrogen atom or a hydrocarbon group R, wherein $R_{10}$ can alternatively be OH or SH, and wherein at least one of $R_9$ and $R_{10}$ is an indicator moiety; wherein the hydrocarbon groups R are independently either unsubstituted or substituted with one or more heteroatoms selected from N, O, S, P, and F or heteroatom groups containing one or more of said heteroatoms.

The invention is also directed to a method for treating a subject afflicted with a disorder characterized by an abnormal or non-optimal Sirt6 or Sirt7 deacylase activity, which includes administering to the subject a modulating compound described above in a pharmaceutically effective amount for treating the disorder.

The invention is also directed to a kit for identifying Sirt6, PfSir2a, or Sirt7 deacylase activity, which includes an acylated substrate, as described above, and a cleavage agent that cleaves the lysine and indicator moiety only when the acylated substrate becomes deacylated. The kit may also include, for example, a sample of Sirt6, PfSir2a, or Sirt7, one or more candidate compounds, candidate compound precursors, one or more acylated substrate precursors, one or more indicator compounds, a quencher, and/or one or more devices for combining reagents and/or testing deacylase activity, such as any of the devices or apparatuses used in performing kinetic measurements for determining enzymatic activity.

DETAILED DESCRIPTION OF THE DISCLOSURE

Figure 1A:
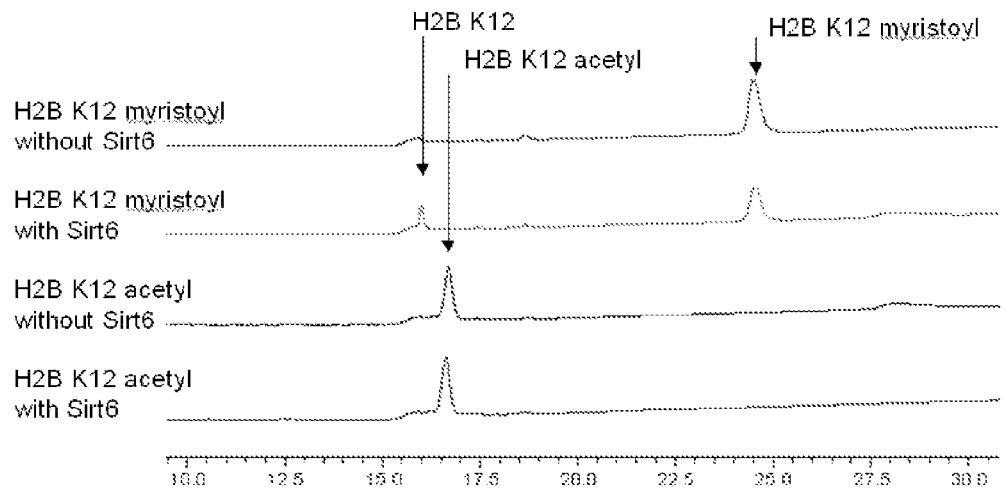
FIGS. 1A, 1B. High-performance liquid chromatography (HPLC) traces for the hydrolysis of acetyl and myristoyl H2B K12 peptides by Sirt6 (A) and HPLC traces for the hydrolysis of acetyl and myristoyl H4 K16 sequences by Sirt6 (B). No hydrolysis of the acetyl peptides was detected, but hydrolysis of the myristoyl peptides was detected.

For convenience, before further description of the present invention, certain terms employed in the specification, examples, and appended claims are described here. These definitions should be read in light of the entire disclosure and as would be understood by a person skilled in the art.

The terms "a" and "an" are used herein to refer to one or to more than one (i.e., to at least one) of the grammatical object of the article. By way of example, "an element" can mean one or more elements, unless otherwise specified.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. In some embodiments, the term "amino acid" refers only to the twenty known essential amino acids, or a subset thereof, i.e., glycine (G), alanine (A), valine (V), leucine (L), isoleucine (I), cysteine (C), methionine (M), phenylalanine (F), tyrosine (Y), tryptophan (W), proline (P), serine (S), threonine (T), asparagine (N), glutamine (Q), aspartic acid (D), glutamic acid (E), histidine (H), lysine (K), and arginine (R). In some embodiments, one or more of any of the foregoing classes or specific types of amino acids are excluded.

The term "polypeptide", and the terms "protein" and "peptide", which are used interchangeably herein, refer to a polymer of amino acids. Exemplary polypeptides include gene products, naturally-occurring proteins, homologs, orthologs, paralogs, fragments, and other equivalents, variants, and analogs of the foregoing. They may include one or more types of any of the amino acid residues described above, or a modified form thereof, and typically include at least 10, 20, 30, 40, or 50, and up to 80, 100, 120, 150, 200, 300, 400, 500, or 1,000 amino acid residues. The term "oligopeptide", as used herein, generally refers to a chain of amino acid residues of at least 4, 5, or 6 and up to 8, 10, 15, or 20. The terms "dipeptide" and "tripeptide" refer, respectively, to two and three linked amino acid residues.

The term "high throughput screening" (HTS) refers to an automated, large-scale method to test small molecule inhibitors for inhibition of a particular enzyme activity or cellular process. HTS typically tests a library of different compounds to determine their activities.

As used herein, the term "modulator" includes any substance that activates or inhibits Sirt6, PfSir2a, or Sirt7 deacylase activity. Moreover, an "activator" is a substance that increases, enhances, or accelerates Sirt6, PfSir2a, or Sirt7 deacylase activity, while an "inhibitor" is a substance that reduces, inhibits, or prevents Sirt6, PfSir2a, or Sirt7 deacylase activity.

The terms "hydrocarbon group", i.e., "hydrocarbon group (R)", and "hydrocarbon linker", as used herein, are, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, or twenty carbon atoms, or a number of carbon atoms within a particular range bounded by any two of the foregoing carbon numbers. Hydrocarbon groups or linkers in different compounds described herein, or in different positions of a compound, may possess the same or different number (or preferred range thereof) of carbon atoms in order to independently adjust or optimize the activity or other characteristics of the compound.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene linker, i.e., —$CH_2$—, or methine linker), ethyl (or ethylene or dimethylene linker, i.e., —$CH_2CH_2$— linker), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups (or their respective linker analogs).

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, 3-methylpentyl, and the numerous $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ saturated and branched hydrocarbon groups. Some examples of branched alkylene linkers are those derived by removal of a hydrogen atom from one of the foregoing exemplary branched alkyl groups (e.g., isopropylene, —$CH(CH_3)$$CH_2$—).

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl (CH$_2$=CH—CH$_2$—CH$_2$—), 2-buten-1-yl (CH$_2$—CH=CH—CH$_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous $C_7$, $C_8$, $C_9$, $C_{10}$, $C_{11}$, $C_{12}$, and higher unsaturated and straight-chained hydrocarbon groups. Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers can alternatively be unsaturated and branched (i.e., branched olefinic or alkenyl groups or linkers). Some examples of branched olefinic groups include propen-2-yl, 3-buten-2-yl (CH$_2$=CH—CH.—CH$_3$), 3-buten-3-yl (CH$_2$=C.—CH$_2$—CH$_3$), 4-penten-2-yl, 4-penten-3-yl, 3-penten-2-yl, 3-penten-3-yl, 2,4-pentadien-3-yl, and the numerous $C_6$, $C_7$, $C_8$, $C_9$, $C_{10}$, $C_{11}$, $C_{12}$, and higher unsaturated and branched hydrocarbon groups. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers may also include one or more heteroatoms (i.e., non-carbon and non-hydrogen atoms), such as one or more heteroatoms selected from oxygen (O), nitrogen (N), sulfur (S), phosphorus (P), and halide atoms, as well as groups containing one or more of these heteroatoms (i.e., heteroatom-containing groups). Some examples of oxygen-containing groups include hydroxy (OH), carbonyl-containing (e.g., carboxylic acid, ketone, aldehyde, carboxylic ester, amide, and urea functionalities), nitro (NO$_2$), carbon-oxygen-carbon (ether), sulfonyl, and sulfinyl (i.e., sulfoxide), and amine oxide groups. The ether group can also be a polyalkyleneoxide group, such as a polyethyleneoxide group. Some examples of nitrogen-containing groups include primary amine, secondary amine, tertiary amine, quaternary amine, cyanide (i.e., nitrile), amide (i.e., —C(O)NR$_2$ or —NRC(O), wherein R is independently selected from hydrogen atom and hydrocarbon group, as described above), nitro, urea, imino, and carbamate, wherein it is understood that a quaternary amine group necessarily possesses a positive charge and requires a counteranion. Some examples of sulfur-containing groups include mercapto (i.e., —SH), thioether (i.e., sulfide), disulfide, sulfoxide, sulfone, sulfonate, and sulfate groups. Some examples of phosphorus-containing groups include organophosphate, organophosphite and organophosphonate groups. Some examples of halide atoms considered herein include fluorine, chlorine, and bromine. One or more of the heteroatoms described above (e.g., oxygen, nitrogen, and/or sulfur atoms) can be inserted between carbon atoms (e.g., as —O—, —NR—, or —S—), or replace a carbon atom (or methylene group) in any of the hydrocarbon groups described above to form a heteroatom-substituted hydrocarbon group or linker. Alternatively, or in addition, one or more of the heteroatom-containing groups can replace one or more hydrogen atoms on the hydrocarbon group or linker.

In particular embodiments, the hydrocarbon group is, or includes, a cyclic or polycyclic group that includes at least one ring heteroatom (for example, one, two, three, four, or higher number of heteroatoms). Such ring heteroatom-substituted cyclic groups are referred to herein as "heterocyclic groups". As used herein, a "ring heteroatom" is an atom other than carbon and hydrogen (typically, selected from nitrogen, oxygen, and sulfur) that is inserted into, or replaces a ring carbon atom in, a hydrocarbon ring structure. In some embodiments, the heterocyclic group is saturated, while in other embodiments, the heterocyclic group is unsaturated (i.e., aliphatic or aromatic heterocyclic groups, wherein the aromatic heterocyclic group is also referred to herein as a "heteroaromatic ring", or a "heteroaromatic fused-ring system" in the case of at least two fused rings, at least one of which contains at least one ring heteroatom). In some embodiments, the heterocyclic group is bound via one of its ring carbon atoms to another group (i.e., other than hydrogen atom and adjacent ring atoms), while the one or more ring heteroatoms are not bound to another group. In other embodiments, the heterocyclic group is bound via one of its heteroatoms to another group, while ring carbon atoms may or may not be bound to another group.

Some examples of saturated heterocyclic groups include those containing at least one oxygen atom (e.g., oxetane, tetrahydrofuran, tetrahydropyran, 1,4-dioxane, 1,3-dioxane, and 1,3-dioxepane rings), those containing at least one nitrogen atom (e.g., pyrrolidine, piperidine, piperazine, imidazolidine, azepane, and decahydroquinoline rings), those containing at least one sulfur atom (e.g., tetrahydrothiophene, tetrahydrothiopyran, 1,4-dithiane, 1,3-dithiane, and 1,3-dithiolane rings), those containing at least one oxygen atom and at least one nitrogen atom (e.g., morpholine and oxazolidine rings), those containing at least one oxygen atom and at least one sulfur atom (e.g., 1,4-thioxane), and those containing at least one nitrogen atom and at least one sulfur atom (e.g., thiazolidine and thiamorpholine rings).

Some examples of unsaturated heterocyclic groups include those containing at least one oxygen atom (e.g., furan, pyran, 1,4-dioxin, and dibenzodioxin rings), those containing at least one nitrogen atom (e.g., pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings), those containing at least one sulfur atom (e.g., thiophene, thianaphthene, and benzothiophene rings), those containing at least one oxygen atom and at least one nitrogen atom (e.g., oxazole, isoxazole, benzoxazole, benzisoxazole, oxazoline, 1,2,5-oxadiazole (furazan), and 1,3,4-oxadiazole rings), and those containing at least one nitrogen atom and at least one sulfur atom (e.g., thiazole, isothiazole, benzothiazole, benzoisothiazole, thiazoline, and 1,3,4-thiadiazole rings).

In some embodiments, any of the generic substituents (e.g., R, $R_1$, $R_2$, and the like) described below may independently exclude any one or more of the classes, subclasses, or particular hydrocarbon groups described above, or may independently include only specific hydrocarbon groups selected from the hydrocarbon groups (R) described above.

The term "acyl" used herein refers to an organic group of the general formula —C(X)R, wherein X is oxygen (=O), sulfur (=S), or amino (=NR) and R independently represents a hydrocarbon group. For purposes of the instant invention, the hydrocarbon group R attached to C(X) possesses at least three carbon atoms connected by carbon-carbon bonds. In different embodiments, the hydrocarbon group R attached to C(X) possesses precisely or at least three, four, five, six, seven, eight, nine, ten, eleven, twelve, thirteen, fourteen, fifteen, sixteen, seventeen, eighteen, nineteen, or twenty carbon atoms, or a number of carbon atoms within a range bounded by any two of the foregoing number of carbon atoms (for example, a carbon number in the range of 3-20, 3-18, 3-16, 3-14, 3-12, 3-10, 3-8, 4-20, 4-18, 4-16, 4-14, 4-12, 4-10, 4-8, 5-20, 5-18, 5-16, 5-14, 5-12, 5-10, 5-8, 6-20, 6-18, 6-16, 6-14, 6-12, 6-10, 6-8, 7-20, 7-18, 7-16, 7-14, 7-12, 7-10, 8-20, 8-18, 8-16, 8-14, 8-12, 9-20, 9-18, 9-16, 9-14, 9-12, 10-20, 10-18, 10-16, 10-14, 10-12, 11-20, 11-18, 11-16, 11-14, 12-20, 12-18, 12-16, 12-14, 13-20, 13-18, 13-16, 14-20, 14-18, or 14-16 carbon atoms).

In one set of embodiments, the hydrocarbon group R attached to C(X) is composed of only carbon and hydrogen atoms. In another set of embodiments, the hydrocarbon group R attached to C(X) is composed of carbon and hydrogen atoms, wherein one or more hydrogen atoms may be substituted by one or more fluoro (F) atoms. In another set of embodiments, the hydrocarbon group R attached to C(X) is composed of carbon and hydrogen atoms, and optionally one or more fluoro atoms, along with one heteroatom selected from O, N, and S that either interrupts a carbon-carbon bond of the hydrocarbon group (R) or replaces a carbon atom (i.e., methylene or methine group) of the hydrocarbon group (R), except that the heteroatom is not included as an OH, SH, or $NH_2$ group, or any charged group, such as alkoxide, sulfide, carboxylate, or ammonium groups, since these types of groups would render the acyl portion too hydrophilic (i.e., not sufficiently hydrophobic). In some embodiments, the hydrocarbon group R attached to C(X) is selected from one or more of straight-chained or branched alkyl, alkenyl, or alkynyl, which may include or exclude one or more heteroatoms; cycloalkyl; aromatic ring; heterocycloalkyl; heteroaromatic; or a hydrocarbon group that includes any one or more of the foregoing substituent classes, such as an alkyl-aromatic, alkyl-heterocyclic, or alkyl-heteroaromatic group. When a heteroatom replaces a carbon atom, the possibility is included that the heteroatom is attached to the carbon of C(X), i.e., as C(X)—O—R, C(X)—S—R, C(X)—NH—R, or C(X)—NR—R, where each instance of an R group is an independent selection.

In one aspect, the invention is directed to a method for identifying a modulator of Sirt6, PfSir2a, or Sirt7 deacylase activity. In a preferred embodiment, the method is practiced in a high throughput screening mode.

Figure 5:
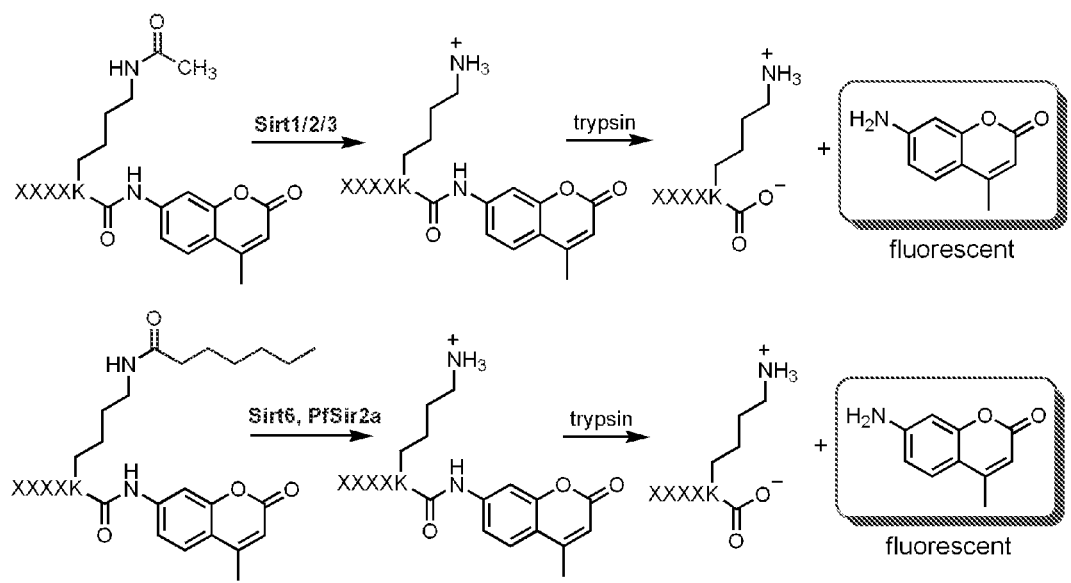
FIG. 5. Schematic drawing comparing the fluorogenic assay for sirtuins (Sirt1, 2, and 3) with robust deacetylase activity and the fluorogenic assay for sirtuins that hydrolyze longer fatty acyl chains (Sirt6 and PfSir2a). K represents a lysine residue in the peptide and X represents any amino acid in the peptide sequence.

In a first part of the method, an acylated substrate (i.e., "substrate") that substantially mimics a hydrophobic acylated lysine residue is contacted with Sirt6, PfSir2a, or Sirt7 in the presence of a candidate compound. In order for the acylated substrate to be effective, the acyl group of the acyl-lysine moiety (i.e., "acyl-lysine mimicking portion") of the substrate is selected as one that is known to be efficiently deacylated by Sirt6, PfSir2a, or Sirt7, as found by any suitable experimental protocol that confirms detectable activity of the Sirt6, PfSir2a, or Sirt7 for a particular substrate (some general procedures for this purpose are shown in FIG. 5). Other structural features aside from the acyl-lysine moiety (e.g., those groups attached to the amino or carboxy terminus of the lysine moiety, or a particular peptide sequence) may be suitably adjusted to provide for a more effective substrate if any such additional features are found to have a significant impact on the level of deacylation activity.

The lysine moiety of the substrate may be derivatized or modified in any suitable manner while preserving its basic amino acid structure. In particular, the side-chain E-aminobutyl group of the lysine moiety can be modified. For example, the lysine moiety can be of the form —NH—CH(R')—C(O)—, where R' is a side-chain, which can be an alkyl or alkenyl chain of one, two, three, four, five, six, seven, eight, nine, or ten carbon atoms terminating in an NH(acyl) or NR(acyl) group. The alkyl or alkenyl chain in R' may also include or exclude one or more heteroatoms selected from N, O, and S, wherein the heteroatom is either inserted between two carbon atoms or replaces a carbon atom (or methylene group), or is in the form of a heteroatom group, such as C(O). Moreover, if the lysine moiety is not part of an oligopeptide or polypeptide structure, the backbone NH(NH terminus) can be attached to a hydrocarbon group (R), or the hydrogen atom of NH substituted with a hydrocarbon group (R), and/or the backbone C(O) can be attached to a hydrocarbon group (R), or a group —OR, or a group —SR, or a group —NHR, or a group —$NR_2$, wherein each R group is independently selected.

The substrate is linked to an indicator moiety. The linkage is a covalent linkage that can be severed by a cleavage agent only after the acyl group on the lysine is removed. In particular embodiments, the covalent linkage is an amide bond formed between the carboxyl terminus of the lysine moiety and an amino group of the indicator compound. The indicator moiety is preferably not linked to the acyl portion of the substrate, since this would likely obviate the very mechanism described herein for generating a signal. When the substrate is contacted with Sirt6, PfSir2a, or Sirt7 under conditions for any of these sirtuins to deacylate the substrate, the removal of the acyl group permits the cleavage agent to cleave the bond between lysine and indicator moiety, thereby releasing the indicator moiety. Release of the indicator moiety results in the generation of a detectable signal. In particular embodiments, the acyl lysine moiety is linked by a peptide bond to at least one other amino acid residue, and the indicator moiety is linked to the lysine bearing the acyl group (particularly if the lysine bearing the acyl group is at a terminal end) or linked to another amino acid, which may be another lysine that is or is not also acylated, particularly if the lysine bearing the acyl group is interiorized, i.e., not at a terminal end.

The cleavage agent can be any substance that can cleave a peptide bond between specific amino acid residues (i.e., the proteolytic cleavage pattern), but incapable of cleaving the peptide bond if an acylated lysine is present. According to one embodiment, a cleavage agent is a proteolytic enzyme, i.e., an enzyme that hydrolyzes a peptide bond (also referred to as a peptidase). Examples of proteolytic enzymes that can function as a cleavage agent include, but are not limited to trypsin, calpain, lysylendopeptidase, endoproteinase Lys-C, metalloendopeptidase, plasmin, carboxypeptidase, chymotrypsin, V8 protease, pepsin, papain, subtilisin, thrombin, elastase, gluc-C, endo lys-C or proteinase K, caspase-1, caspase-2, caspase-3, caspase-4, caspase-5, caspase-6, caspase-7, caspase-8, MetAP-2, adenovirus protease, HIV protease, and the like.

In a specific embodiment, the cleavage agent is trypsin. Trypsin will cleave peptides attached to the carboxy terminus of the lysine residue of the substrate. Another suitable cleavage agent is pepsin, which hydrolyzes peptide bonds on the amino termini of phenylalanine, tryptophan, and tyrosine residues; thus, pepsin will cleave a substrate peptide between a lysine residue and an adjacent phenylalanine, tryptophan, or tyrosine residue.

The indicator moiety is any molecule that is detectable once cleaved from the substrate. In one embodiment, the indicator moiety is a fluorophore. Some common fluorophores include fluorescein isothiocyanate (FITC), derivatives of rhodamine (TRITC), coumarin, pyrene, cyanine, maleimide derivative dyes, CF dyes, the FluoProbes dyes, the DyLight Fluors, the Oyester dyes, the Atto dyes, the HiLyte Fluors, luciferins, and the Alexa Fluors. Luciferins, such as firefly luciferin, can emit light when incubated with firefly luciferase and ATP. In particular embodiments, the indicator moiety is an aminocoumarin fluorophore, or more specifically, an aminomethylcoumarin fluorophore, such as 7-amino-4-methylcoumarin (AMC).

In some embodiments, fluorescence intensity or emission wavelength of the fluorophore is dependent on the presence or absence of a linkage between the fluorophore and the substrate. The change in fluorescence intensity or emission wavelength of the fluorophore (i.e., as compared before and after cleavage from the substrate) is typically measured with a fluorescence spectrophotometer.

In other embodiments, the fluorophore attached to the substrate does not necessarily change in fluorescence intensity or emission wavelength depending on the presence or absence of a linkage between the fluorophore and the substrate, but a detectable signal is instead provided by also labeling the substrate with a quenching group. For example, the fluorophore can be attached to the carboxyl terminus of the acylated lysine, while the quenching group can be attached to a different amino acid in a peptide chain or other portion of the molecular structure containing the acylated lysine. Prior to cleavage of the fluorophore or quenching group, the fluorescence intensity of these substrates is low due to the close proximity of the quenching group to the fluorophore. After cleavage of either the fluorophore or quenching group from the substrate, the fluorescence intensity is enhanced. This allows measurement of the quantity of the cleaved substrate peptide. Examples of quenching groups suitable for use herein include DNP, Black Hole Quencher™ moieties, and DABCYL. In some embodiments, the quencher may also be a fluorophore.

In some embodiments, the substrate contains a donor-acceptor pair of fluorophores, as commonly used in fluorescence energy transfer (FRET) experiments. Prior to the cleavage of either the donor or acceptor fluorophores, the donor and acceptor fluorophores are in close enough proximity for energy transfer between the donor and acceptor, where such energy transfer can be measured by FRET. One fluorophore can be linked, for example, to the carboxyl terminus of the acylated lysine, and the other member of the donor-acceptor pair placed in close proximity, e.g., attached to another portion of the substrate, such as another amino acid residue of the substrate, or on another portion of the lysine residue, such as on the lysine side chain. When one of the fluorophores of the pair is detached, the FRET signal intensity is significantly diminished, which can be correlated with an activity level for Sirt6, PfSir2a, or Sirt7.

The candidate compound can be any molecule or macromolecule (e.g., a protein, polynucleotide, or polysaccharide) being tested for its ability to inhibit, activate, or otherwise modulate Sirt6, PfSir2a, or Sirt7 deacylase activities. In particular embodiments, the candidate compound contains a hydrophobic acyl-lysine mimicking portion, as described above for the substrate, except that the candidate compound is not required to include an indicator moiety (or excludes an indicator moiety). Without being bound by any theory, an effective candidate compound is believed to form a stalled covalent intermediate with Sirt6, PfSir2a, or Sirt7. Therefore, any structural features that can encourage this interaction with Sirt6, PfSir2a, or Sirt7 may be included in the candidate compound in an effort to make the candidate compound a more effective modulator.

In one embodiment, the candidate compound is a small molecule. A "small molecule" refers to small organic compounds, such as heterocycles, peptides, saccharides, steroids, and the like. The small molecule modulators preferably have a molecular weight of less than or up to about 5000, 3000, 1500 Daltons, 1000 Daltons, 800 Daltons, or even less than about 500 Daltons. The compounds may be modified to enhance, for example, efficacy, stability, or pharmaceutical compatibility.

After cleavage of the indicator moiety, the signal intensity generated by the cleavage reaction is detected. By methods known in the art for correlating a signal intensity with enzymatic activity, the signal intensity generated by the cleavage reaction is correlated with Sirt6, PfSir2a, or Sirt7 deacylase activity. The observed deacylase activity, which occurs in the presence of the candidate compound, is compared with deacylase activity of the same sirtuin under the same or substantially same conditions except in the absence of the candidate compound (i.e., the control deacylase activity). The control deacylase activity value may be obtained by performing a separate experiment in which the acylated substrate is contacted with Sirt6, PfSir2a, or Sirt7, in the absence of a candidate compound, under conditions for Sirt6, PfSir2a, or Sirt7 to deacylate the substrate, contacting the deacylated substrate with a cleavage agent, and observing a signal intensity. The experiment for determining the control deacylase activity value may be included as another step of the instant method conducted directly prior to or after the above-described method that includes the candidate compound. Alternatively, the control deacylase activity value may already be known from a previous experiment, and thus, not required to be re-established in the above method.

If no difference is found between the control deacylase activity value and the deacylase activity value observed in the presence of the candidate compound, it can be concluded that the candidate compound is not a modulator of Sirt6, PfSir2a, or Sirt7. Conversely, if a difference is found between the control deacylase activity value and the deacylase activity value observed in the presence of the candidate compound, it can be concluded that the candidate compound is a modulator of Sirt6, PfSir2a, or Sirt7. A candidate compound is identified as a Sirt6, PfSir2a, or Sirt7 inhibitor when there is a decrease in Sirt6, PfSir2a, or Sirt7 deacylase activity in the presence of the candidate compound, relative to Sirt6, PfSir2a, or Sirt7 deacylase activity in the absence of the candidate compound. A candidate compound is identified as a Sirt6, PfSir2a, or Sirt7 activator when there is an increase in Sirt6, PfSir2a, or Sirt7 deacylase activity in the presence of the candidate compound, relative to Sirt6, PfSir2a, or Sirt7 deacylase activity in the absence of the candidate compound.

To perform an assay for detecting Sirt6, PfSir2a, or Sirt7 activity, a sample containing Sirt6, PfSir2a, or Sirt7 is first brought into contact with a suitable substrate described herein and incubated under appropriate conditions. The term "sample" refers to any sample of interest that contains purified, partially purified, or unpurified Sirt6, PfSir2a, or Sirt7, and can be a lysate from cells or tissues, or a preparation of Sirt6, PfSir2a, or Sirt7 protein (purified from cells or tissues or a recombinant expression system). Following the incubation period between a Sirt6, PfSir2a, or Sirt7 sample and a substrate, a cleavage agent is added to the reaction along with an appropriate reaction buffer. Following this second incubation period, the reaction can be diluted with water or other neutral-pH buffer, and fluorescence is recorded by a fluorescence detector that detects fluorescence at appropriate excitation and detection wavelengths for the fluorophore used. The signal intensity is then correlated with Sirt6, PfSir2a, or Sirt7 activity. Alternatively, the cleavage agent is present at the time the acylated substrate is in the presence of Sirt6, PfSir2a, or Sirt7 and the candidate compound, and thus, a second step is not needed for the cleavage reaction.

In some embodiments, the assays are performed in a microplate format. For example, a substrate peptide can be added to a reaction buffer, and the solution poured into wells of a microplate for fluorometry, and the plate then incubated. If the effect of a candidate compound is to be observed, the candidate compound can be included with the substrate. Next, an aliquot of a Sirt6, PfSir2a, or Sirt7 sample is added to each well, and subjected to deacylation for a given length of time. Subsequently or at the same time, an aliquot of proteolytic enzyme and an appropriate reaction buffer is added to each well, and then the fluorescence intensity of the solution is measured periodically, using a fluorescence microplate reader.

The assays can be miniaturized and automated for high-throughput analysis. The assays can also be performed in one or more separate containers; however, one of the benefits of the disclosed assays is the ability of the assays to be carried out in a single container, such as a microplate well, which allows for ease of use and automation. The substrate may optionally be immobilized on a solid material, such as by biotin-streptavidin linkage, in situations where such immobilization is desired.

Another assay provided herein is a liquid chromatography-mass spectrometry (LCMS) assay. In this assay, Sirt6, PfSir2a, or Sirt7 activity is identified by determining of the amounts of the substrate peptide and product peptide following contact with Sirt6, PfSir2a, or Sirt7. The quantification can be achieved by using the area of ultraviolet light absorption (such as at 215 nm or 280 nm) for the product peak and substrate peak on the LC chromatogram, or by using the ion intensity of the product ion and substrate ion in the mass spectrometry. Comparison of the amount of substrate (e.g., acylated peptide) to product (i.e., deacylated peptide) correlates with the amount of Sirt6, PfSir2a, or Sirt7 activity on the substrate. In this assay, an increase in the amount of product indicates Sirt6, PfSir2a, or Sirt7 activity, and little or no product indicates little or no Sirt6, PfSir2a, or Sirt7 activity.

Using a mass spectrometry assay, a candidate compound can be identified as a Sirt6, PfSir2a, or Sirt7 inhibitor or activator as follows. A candidate compound is identified as a Sirt6, PfSir2a, or Sirt7 inhibitor when there is a decrease in product (e.g., deacylated peptide) produced in the presence of the candidate compound relative to product produced in the absence of the candidate compound. A candidate compound is identified as a Sirt6, PfSir2a, or Sirt7 activator when there is an increase in product (e.g., deacylated peptide) produced in the presence of the candidate compound relative to product produced in the absence of the candidate compound. Preferably, in order for the candidate compound to be considered a modulator, the difference in activity between the presence and absence of the candidate compound should be at least 20%, 30%, 40%, 50%, 60%, 70%, 80%, 90%, 100%, 200%, 300%, 400%, 500% or greater.

In some embodiments, to avoid shortage of the substrate relative to the predicted Sirt6, PfSir2a, or Sirt7 enzyme activity, an excess amount of the substrate is used in the assay. Specifically, in order to determine the Sirt6, PfSir2a, or Sirt7 activity in a general biological sample, such as cell nuclear extract, the concentration of the substrate to be used in the reaction is typically 1 to 200 µM, and preferably 20 to 50 µM. The concentration of the cleavage agent can also be adjusted depending on the quantity of substrate used. Typically, the amount of the cleavage agent is adjusted according to the predicted quantity of the generated substrate peptide so as to realize enough cleavage of the substrate peptide under a given condition. In particular embodiments, when substrate at a concentration of about 0.01 to 1 mM is used in the reaction, the quantity of trypsin to be used can be, for example, 0.2 to 5 µg per 60 µL reaction, preferably 1 to 2 µg per 60 µL reaction.

With respect to the first reaction (deacylation by Sirt6, PfSir2a, or Sirt7), the pH for the reaction can be selected by taking the optimal pH of Sirt6, PfSir2a, or Sirt7 into consideration. The pH is typically adjusted to a pH of 6.0 to 8.5, or more particularly, a pH of 6.8 to 8.5. The reaction buffer preferably provides the above-mentioned pH. For example, Tris-HCl, HEPES-KOH, and other such buffers may be used in the instant method. More specifically, for example, 20 mM Tris-HCl having a pH of 7.4 can be used. Generally, NAD is a co-substrate required for Sirt6, PfSir2a, or Sirt7 functioning, and is typically used at about 0.5 mM concentration. Salts and preservatives are generally also included in the reaction solution. For example, 1 mM dithiothreitol (DTT) can be added to the reaction. The first reaction (deacylation by Sirt6, PfSir2a, or Sirt7) can be incubated between 2-20 hours at 35-40° C. Specific exemplary incubation conditions include, for example, incubating a liquid mixture of a substrate and a Sirt6-, PfSir2a-, or Sirt7-containing sample in Tris-HCl buffer (pH 7.4, about 20 mM) containing NAD (about 0.5 mM) and DTT (about 1 mM) for about 4 hours at about 37° C. For the second reaction by a cleavage agent, the cleavage agent is added to the reaction along with an appropriate reaction buffer. For example, trypsin (1 µg) and $CaCl_2$ (1 mM) can be added and the reaction incubated for approximately 3 hours at about 37° C.

Following trypsin incubation, the reaction can be diluted with water or other neutral-pH buffer, and fluorescence is recorded by a fluorescence detector that detects fluorescence at appropriate excitation and detection wavelengths for the fluorophore used. The signal intensity is then correlated with Sirt6, PfSir2a, or Sirt7 activity as discussed above.

In particular embodiments, the candidate compound, which may ultimately be confirmed to be a modulator of Sirt6, PfSir2a, or Sirt7, is a compound within the following generic chemical structure:

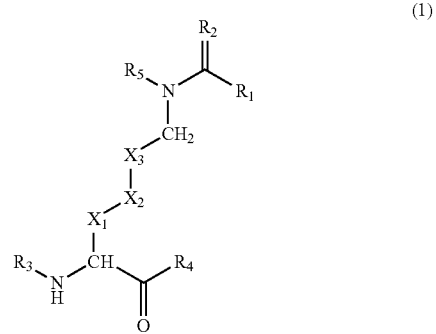

(1)

In Formula (1), $R_1$ is a hydrocarbon group having at least three carbon atoms connected by carbon-carbon bonds. The group $R_2$ is selected from S, $NR_6$, and O, wherein $R_6$ is a hydrogen atom or any of the substituted or unsubstituted hydrocarbon groups R described above, or a selection thereof. The linking groups $X_1$, $X_2$, and $X_3$ are independently selected from —(CH$_2$)$_n$—, —NR$_{12}$—, —O—, —S—, or a bond, wherein R$_{12}$ is a hydrogen atom or any of the substituted or unsubstituted hydrocarbon groups R described above, or a selection thereof. The subscript n independently represents 1, 2, or 3. In particular embodiments, X$_1$, X$_2$, and X$_3$ are each selected from —(CH$_2$)$_n$—, wherein n is independently 1, 2 or 3, or wherein n is independently 1 or 2, or wherein n is 1 for all of X$_1$, X$_2$, and X$_3$. The group R$_5$ is a hydrogen atom or any of the substituted or unsubstituted hydrocarbon groups R described above, or a selection thereof. The groups R$_3$ and R$_4$ are independently hydrogen atom or any of the substituted or unsubstituted hydrocarbon groups R described above, or a selection thereof, wherein R$_4$ can alternatively be OH, NH$_2$, or SH. In some embodiments, one or both of R$_3$ and R$_4$ are non-biological (i.e. synthetic) groups containing at least 1, 2, 3, 4, or 5 and up to 10, 15, 20, 25, 30, 40, or 50 non-hydrogen atoms. In other embodiments, one or both of R$_3$ and R$_4$ are biologically related groups, such as an amino acid, dipeptide, tripeptide, oligopeptide, polypeptide (e.g., protein, including an enzyme, antibody, or receptor), nucleobase, nucleoside, nucleotide, dinucleotide, oligonucleotide, polynucleotide, monosaccharide, disaccharide, oligosaccharide, polysaccharide, biotin, avidin, streptavidin, or ligand, any of which may be a small molecule, or a macromolecule containing hundreds of non-hydrogen atoms. In some embodiments, one or both of R$_3$ and R$_4$ contribute to the modulation of Sirt6, PfSir2a, or Sirt7 or provide an important function when the modulating compound is administered to a subject, e.g., R$_3$ and/or R$_4$ may make the modulator more bioavailable, function to target a receptor, or function as an adjuvant drug moiety.

In different embodiments under Formula (1), R$_1$ is a hydrocarbon group possessing precisely or at least three, four, five, six, seven, eight, nine, ten, eleven, twelve, thirteen, fourteen, fifteen, sixteen, seventeen, eighteen, nineteen, or twenty carbon atoms, or a number of carbon atoms within a range bounded by any two of the foregoing number of carbon atoms (for example, a carbon number in the range of 3-20, 3-18, 3-16, 3-14, 3-12, 3-10, 3-8, 4-20, 4-18, 4-16, 4-14, 4-12, 4-10, 4-8, 5-20, 5-18, 5-16, 5-14, 5-12, 5-10, 5-8, 6-20, 6-18, 6-16, 6-14, 6-12, 6-10, 6-8, 7-20, 7-18, 7-16, 7-14, 7-12, 7-10, 8-20, 8-18, 8-16, 8-14, 8-12, 9-20, 9-18, 9-16, 9-14, 9-12, 10-20, 10-18, 10-16, 10-14, 10-12, 11-20, 11-18, 11-16, 11-14, 12-20, 12-18, 12-16, 12-14, 13-20, 13-18, 13-16, 14-20, 14-18, or 14-16 carbon atoms).

In one set of embodiments under Formula (1), the hydrocarbon group R$_1$ is composed of only carbon and hydrogen atoms. In another set of embodiments, the hydrocarbon group R$_1$ is composed of carbon and hydrogen atoms, wherein one or more hydrogen atoms may be substituted by one or more fluoro (F) atoms. In another set of embodiments, the hydrocarbon group R$_1$ is composed of carbon and hydrogen atoms, and optionally one or more fluoro atoms, along with one heteroatom selected from O, N, and S that either interrupts a carbon-carbon bond of the hydrocarbon group R$_1$ or replaces a carbon atom (i.e., a methylene or methine group) of the hydrocarbon group R$_1$, except that the heteroatom is not included as an OH, SH, or NH$_2$ group, or any charged group, such as alkoxide, sulfide, carboxylate, or ammonium groups, since these types of groups would render the acyl portion too hydrophilic (i.e., not sufficiently hydrophobic). The result can be, for example, an ether (R—O—R), thioether (R—S—R), secondary amine (R—NH—R), or tertiary amine (R—NR—R) in R$_1$, wherein the R groups in each case are independently selected. In some embodiments, the hydrocarbon group R$_1$ is selected from one or more of straight-chained or branched alkyl, alkenyl, or alkynyl, which may include or exclude one or more heteroatoms; cycloalkyl; aromatic ring; heterocycloalkyl; heteroaromatic; or a hydrocarbon group that includes any one or more of the foregoing substituent classes, such as an alkyl-aromatic, alkyl-heterocyclic, or alkyl-heteroaromatic group. When a heteroatom replaces a carbon atom, the possibility is included that the heteroatom is attached to the carbon of C(=R$_2$), i.e., as C(=R$_2$)—O—R$_1$, C(=R$_2$)—S—R$_1$, C(=R$_2$)—NH—R$_1$, or C(=R$_2$)—NR—R$_1$. In some embodiments, one or more of the latter possibilities are excluded.

In particular embodiments of Formula (1), R$_2$ is S, thus resulting in a sub-generic set of candidate (or modulator) compounds of the following formula:

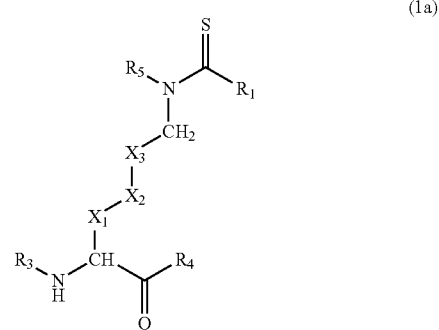

(1a)

In other particular embodiments of Formula (1), R$_2$ is O, thus resulting in a sub-generic set of candidate (or modulator) compounds of the following formula:

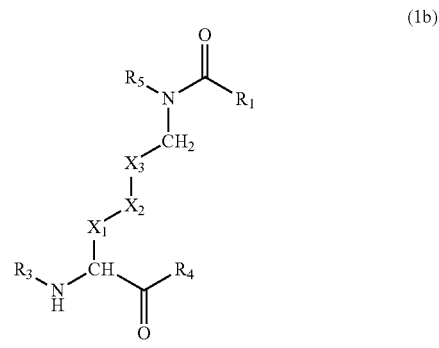

(1b)

In other particular embodiments of Formula (1), R$_2$ is NR$_6$, thus resulting in a sub-generic set of candidate (or modulator) compounds of the following formula:

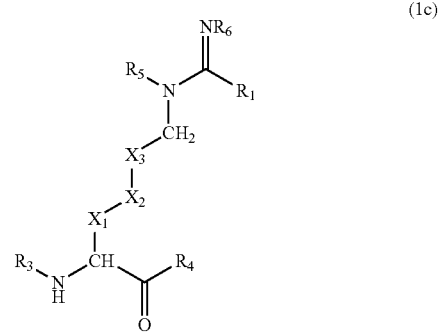

(1c)

The substrate may also be delineated by any of the chemical structures encompassed by Formulas (1), (1a), (1b), or (1c), except that at least one indicator is included. Preferably, at least one of $R_3$ and $R_4$ is or includes an indicator moiety. For convenience, and to firmly establish that the structures of the substrate and candidate (or modulator) compounds are different when used in the assay method, the following separate generic structural formula is provided for delineating an exemplary set of substrate compounds:

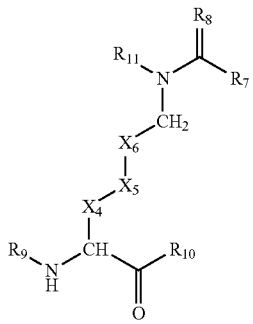

(2)

In Formula (2), the meaning of $R_7$ is as specified for $R_1$ in Formula (1) above, the meaning of $R_8$ is as specified for $R_2$ in Formula (1) above, the meaning of $R_9$ is as specified for $R_3$ in Formula (1) above, the meaning of $R_{10}$ is as specified for $R_4$ in Formula (1) above, the meaning of $R_{11}$ is as specified for $R_5$ in Formula (1) above, and the meanings of $X_4$, $X_5$, and $X_6$ are as specified for $X_1$, $X_2$, and $X_3$, respectively, in Formula (1) above, except that at least one indicator moiety is included in any generic substituent shown in Formula (2), where preferably, at least one of $R_9$ and $R_{10}$ is an indicator moiety. Furthermore, for the purpose of distinguishing candidate and substrate structures, $NR_6$ specified under $R_2$ in Formula (1) is designated as $NR_{13}$ under $R_8$ of Formula (2). Similarly, $NR_{12}$ specified under $X_1$, $X_2$, and $X_3$ under Formula (1) is designated as $NR_{14}$ under $X_4$, $X_5$, and $X_6$ of Formula (2). In particular embodiments, one of $R_9$ and $R_{10}$ is an indicator moiety and one of $R_9$ and $R_{10}$ is or contains at least one amino acid residue or is a dipeptide, tripeptide, oligopeptide, or protein.

In particular embodiments of Formula (2), $R_8$ is S, thus resulting in a sub-generic set of substrate compounds of the following formula:

(2a)

In other particular embodiments of Formula (2), $R_8$ is O, thus resulting in a sub-generic set of substrate compounds of the following formula:

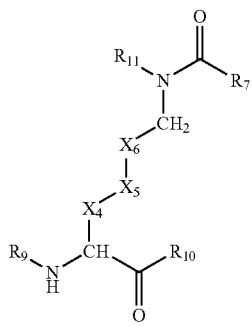

(2b)

In other particular embodiments of Formula (2), $R_8$ is $NR_{13}$, thus resulting in a sub-generic set of substrate compounds of the following formula:

(2c)

In some embodiments, the substrate, the candidate compound, or both, have $R_3$, $R_4$, $R_9$, and/or $R_{10}$ as amide-linked moieties, typically peptide or peptide-mimicking moieties. In particular embodiments, the amide-linked moieties exclude one or more non-amide linkages or groups, such as thioamide, thiourea, sulfonamide, sulfone, sulfamide, sulfoxide, organoester (i.e., —C(O)O—), organothioester (i.e., —C(S)O—), urea, ether (i.e., R—O—R), thioether (i.e., R—S—R), disulfide, azo, carbamate (i.e., —OC(O)NH—), carbonate (i.e., —OC(O)O—), imine, phosphate, phosphonate, phosphinate, and phosphine oxide linkages or groups. In other particular embodiments, the groups that are excluded are hydrolyzable groups, or groups that would undergo hydrolysis or cleavage when introduced into cellular tissue. In some embodiments, one or more such groups may be included if such hydrolysis is desired, or to endow the molecule with other improved properties, such as an improved targeting ability, biodistribution, or bioavailability.

Methods to synthesize the substrates and candidate (or modulator) compounds described herein are known in the art, and as described in the Examples that follow. For example, the coupling of acyl groups to lysine side chains can be accomplished using well known reaction conditions for the preparation of amides from amines and carboxylic acids. Moreover, the conversion of a carbonyl oxygen atom (i.e., $R_2$ or $R_8$) to a thiocarbonyl can be accomplished by, for example, reaction with Lawensson reagent by methods well known in the art.

The ability of a candidate compound to inhibit Sirt6, PfSir2a, or Sirt7 activity is measured by determining the $IC_{50}$ of the candidate compound. As used herein, "$IC_{50}$" or "half maximal inhibitory concentration" identifies how much of a compound is needed to inhibit activity by half. The $IC_{50}$ of a compound can be determined by constructing a dose-response curve and examining the effect of different concentrations of a compound on reducing or preventing enzymatic activity. $IC_{50}$ values can be calculated for a given inhibitor by determining the concentration needed to inhibit half of the maximum enzymatic activity. The mathematical analysis used for deriving an $IC_{50}$ value is well known in the art.

The ability of a candidate compound to activate Sirt6, PfSir2a, or Sirt7 activity is measured by determining the $EC_{50}$ of the candidate compound. As used herein, "$EC_{50}$" or "half maximal effective concentration" refers to the concentration of a compound that induces a response halfway between the baseline and maximum. The $EC_{50}$ of a graded dose-response curve therefore represents the concentration of a compound where 50% of its maximal effect is observed. The mathematical analysis used for deriving an $EC_{50}$ value is well known in the art.

The Sirt6, PfSir2a, or Sirt7 inhibitors of the invention preferably inhibit Sirt6, PfSir2a, or Sirt7 deacylase activity with an $IC_{50}$ or $EC_{50}$ less than or equal to 1 µM, 2 µM, 5 µM, 10 µM, 20 µM, 30 µM, 40 µM, 50 µM, or 100 µM, or an $IC_{50}$ or $EC_{50}$ value within a range bounded by any two of these values.

In another aspect, the invention is directed to a kit useful for measuring the activity of Sirt6, PfSir2a, or Sirt7 in a sample, and for screening compounds that inhibit or enhance the Sirt6, PfSir2a, or Sirt7 activity described above. The kit contains, at minimum, a substrate or substrate precursor that includes an acylated lysine or mimic thereof, as described hereinabove. The kit can also include one or more of the following components: one or more samples of Sirt6, PfSir2a, or Sirt7; a cleavage agent, as described above; one or more candidate compounds or candidate compound precursors; one or more indicator compounds; a quencher; a buffer; a protein-stabilizing or protein-denaturation component, such as BSA or a polyol, such as sucrose or fructose; and one or more devices for combining reagents and/or testing deacylase activity, such as any of the devices or apparatuses used in performing kinetic measurements for determining enzymatic activity.

In another aspect, the invention is directed to a pharmaceutical composition that includes one or more of the Sirt6-, PfSir2a-, or Sirt7-modulating compounds described above dispersed in one or more physiologically acceptable carriers or excipients. The phrase "pharmaceutically acceptable excipient" or "pharmaceutically acceptable carrier", as used herein refers to a pharmaceutically acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic composition for administration to the subject. Each excipient should be "acceptable" in the sense of being compatible with the other ingredients of the formulation and physiologically safe to the subject.

The pharmaceutical composition is useful in treating or preventing a disorder characterized by an abnormal or non-optimal Sirt6, PfSir2a, or Sirt7 deacylase activity. The Sirt6-, PfSir2a-, or Sirt7-modulating compound in the pharmaceutical composition can also be a physiologically acceptable salt or solvate of any of the modulator compounds described above. Acceptable salts and solvates can be made by any of the techniques known in the art. As known in the art, a salt can be produced by reacting a basic portion (e.g., amino) of the active compound with a Bronsted acid, such as HCl or $H_2SO_4$, or with a Lewis acid, such as $CH_3Br$. If desired, the initially introduced anion or cation can be exchanged with another anion or cation. As also known in the art, a solvate can be produced by dissolving or otherwise treating the active compound with a solvent under conditions where one, two, or more solvent molecules remain associated with each molecule of the active ingredient.

In another aspect, the invention is directed to methods for treating or preventing a disorder characterized by an abnormal or non-optimal Sirt6, PfSir2a, or Sirt7 deacylase activity. The methods include administering to a subject a Sirt6, PfSir2a, or Sirt7 modulator in a pharmaceutically effective amount, i.e., an amount that treats or prevents the disorder in a desired manner.

The disorder, which can be a disease or condition, may be, for example, a fatty liver disease, obesity, diabetes, neurodegenerative disease (e.g., Parkinson's, Alzheimer's, and Huntington's), cardiovascular disease (e.g., atherosclerosis), blood clotting disorder, inflammation, or an inflammatory disorder or condition (e.g., rheumatoid arthritis). Alternatively, the disorder can be related to, associated with, caused by, or causative for a fatty liver disease, obesity, or diabetes. In the particular case of PfSir2a, inhibition of the deacylation activity of PfSir2a can be used for treating a subject afflicted with malaria since PfSir2a is a sirtuin specific to the malaria parasite and is important for the malaria parasite's antigenic variation, which is a process the parasite uses to evade the host's immune response. The method of treatment includes administering to a subject in need thereof a pharmaceutically effective (i.e., therapeutically effective) amount of a Sirt6, PfSir2a, or Sirt7 modulator.

As is well known in the art, the dosage of the active ingredient(s) significantly depends on such factors as the disorder or condition being treated, the extent of the disorder or condition, the method of administration, size of the patient, and potential side effects. In different embodiments, depending on these and other factors, a suitable dosage of the Sirt6, PfSir2a, or Sirt7 modulator and/or other active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day for a total treatment time of one, two, three, four, or five days, and up to, for example, one, two, three, or four weeks. Alternatively, or in addition, the composition is administered until a desired change in the disorder or condition is realized.

In certain embodiments, the Sirt6-, PfSir2a-, or Sirt7-modulating compounds described herein may be taken alone, while in other embodiments they are taken in combination with one or more other compounds that may or may not also function to modulate Sirt6, PfSir2a, or Sirt7 or favorably augment or modify the activity of the Sirt6-, PfSir2a-, or Sirt7-modulating compound. In one embodiment, a mixture of two or more Sirt6-, PfSir2a-, or Sirt7-modulating compounds may be administered to a subject in need thereof. In another embodiment, one or more Sirt6-, PfSir2a-, or Sirt7-modulating compounds may be administered with one or more therapeutic agents for the treatment or prevention of a disorder related to an abnormal or non-optimal Sirt6, PfSir2a, or Sirt7 deacylase activity. In some embodiments, the one or more therapeutic agents are administered at the same time as the Sirt6-, PfSir2a-, or Sirt7-modulating compound (e.g., as a pharmaceutical composition containing the one or more therapeutic agents and Sirt6-, PfSir2a-, or Sirt7-modulating compound), while in another embodiment, the one or more therapeutic agents are administered separately from the Sirt6-, PfSir2a-, or Sirt7-modulating compound. When using separate formulations, the Sirt6-, PfSir2a-, or Sirt7-modulating compound may be administered at the same, intermittent, staggered, prior to, or subsequent to the administration of another therapeutic agent.

Any of the Sirt6-, PfSir2a-, or Sirt7-modulating compounds described herein can be made or modified to have improved properties for administration to a mammalian subject, e.g., to improve stability, cell penetrating ability, longer lifetime, and the like. For example, to enhance cell permeability of the substrate, the modulator can include a peptide chain containing a string of multiple amino acids, such as 8-10 arginine or chemically similar residues, or a polyalkyleneoxide chain, such as a polyethylene glycol (PEG) chain having 2, 3, 4, 5, 6, 7, 8, 9, 10, or a higher number of ethylene oxide units.

Sirt6-, PfSir2a-, or Sirt7-modulating compounds and their physiologically acceptable salts and solvates may be administered (and suitably formulated therefore) by, for example, injection (e.g. SubQ, 1M, 1P, 1V), inhalation or insufflation (either through the mouth or the nose) or oral, buccal, sublingual, transdermal, nasal, parenteral or rectal administration. In one embodiment, a Sirt6-, PfSir2a-, or Sirt7-modulating compound may be administered locally, at the site where the target cells are present, i.e., in a specific tissue, organ, or fluid (e.g., blood, cerebrospinal fluid, etc.). Sirt6-, PfSir2a-, or Sirt7-modulating compounds can be formulated for a variety of modes of administration, including systemic and topical or localized administration. Techniques and formulations are well known in the art, much of which can be found, for example, in Remington's Pharmaceutical Sciences, Meade Publishing Co., Easton, Pa.

Pharmaceutical compositions (including cosmetic preparations) may comprise from about 0.00001 to 100%, such as from 0.001 to 10% or from 0.1% to 5% by weight of one or more Sirt6-, PfSir2a-, or Sirt7-modulating compounds described herein. In certain topical formulations, the active agent is present in an amount in the range of approximately 0.25 wt. % to 75 wt. % of the formulation, or in the range of approximately 0.25 wt. % to 30 wt. % of the formulation, or in the range of approximately 0.5 wt. % to 15 wt. % of the formulation, or in the range of approximately 1.0 wt. % to 10 wt. % of the formulation.

Toxicity and therapeutic efficacy of Sirt6-, PfSir2a-, or Sirt7-modulating compounds can be determined by standard pharmaceutical procedures in cell cultures or experimental animals. The $LD_{50}$ is the dose lethal to 50% of the population. The dose ratio between toxic and therapeutic effects ($LD_{50}/ED_{50}$) is the therapeutic index. Sirt6-, PfSir2a-, or Sirt7-modulating compounds that exhibit large therapeutic indexes are preferred. While Sirt6-, PfSir2a-, or Sirt7-modulating compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

Examples have been set forth below for the purpose of illustration and to describe the best mode of the invention at the present time. However, the scope of this invention is not to be in any way limited by the examples set forth herein.

EXAMPLES

Reagents and Instrumentation

Reagents were generally obtained from Aldrich or Acros in the highest purity available and used as supplied.

Synthesis of Substrates

Typically, α-Fmoc-(ε-acyl)-lysine (0.2 mmol) was first coupled to trityl choloride resin (100 mg, 0.1 mmol). The following peptide synthesis was based on using standard Fmoc/tBu chemistry O-benzotriazol-N,N,N',N'-tetramethyluronium hexafluorophosphate/1-hydroxybenzotriazol (HBTU/HOBt) protocol. For cleavage of the peptide from the resin, resin was suspended in a 1:1:8 by volume mixture of acetic acid/TFE/DCM for 30 min at RT. The resin was filtered and the filtrate was concentrated under vacuum. The excess of acetic acid was removed as an azeotrope with hexane to give protected peptides with free carboxylic acid. The residue was dissolved in a solution of dichloromethane (2 mL) with pyridine (50 μL). AMC (7-amino-4-methylcoumarin, 63 mg, 0.36 mmol) and DCC(N,N'-Dicyclohexylcarbodiimide, 64 mg, 0.31 mmol) were added to the above mixture. After stirring at room temperature (RT) overnight, the reaction was filtered and concentrated under vacuum. For removal of the protecting groups, the above residue was treated with TFA (2 mL) for 4 hours. The crude peptides were purified by reverse phase HPLC on BECKMAN COULTER System Gold 125P solvent module & 168 Detector with a TARGA C18 column (250×20 mm, 10 μm, Higgins Analytical, Inc., Mountain View, Calif.) monitoring at 215 nm. Mobile phases used were 0.1% aqueous TFA (solvent A) and 0.1% TFA in acetonitrile (solvent B). Peptides were eluted with a flow rate of 10 mL/min with the following gradient: 0% solvent B for 5 min, then 0% to 25% solvent B over 25 min. The identity and purity of the peptides were verified by LCMS. ISGASE(acetyl-K)-AMC peptide: LCMS (ESI) calculated for $C_{40}H_{59}N_9O_{14}$ [MH$^+$] 890.4, observed 890.5. ISGASE(butyryl-K)-AMC peptide: LCMS (ESI) calculated for $C_{42}H_{63}N_9O_{14}$ [MH$^+$] 918.4, observed 918.5. ISGASE(heptanoyl-K)-AMC peptide: LCMS (ESI) calculated for $C_{45}H_{69}N_9O_{14}$ [MH$^+$] 906.5, observed 906.4. ISGASE(myristoyl-K)-AMC peptide, LCMS (ESI) calculated for $C_{52}H_{83}N_9O_{14}$ [MH$^+$] 1058.6, observed 1058.6.

Synthesis of a Candidate Compound $P_4S_{10}$ (0.1 mol) and Methanol (0.72 mol) were added into 1,2-dichlorobenzene (100 ml) at 40° C. The mixture was then heated to 120° C. for 5 mins and then to 178° C. for 10 mins. The mixture was cooled to 100° C., then myristic acid (0.3 mol) was added. and the reaction mixture was heated to 178° C. for 10 mins. The reaction mixture was then cooled down to 130° C. and more $P_4S_{10}$ (0.05 mol) was added. The reaction mixture was then heated to 160° C. for 5 mins. After filtration to get rid of the precipitation, methyl dithiomyristate was obtained as a clear yellow liquid by vacuum distillation of the filtrate.

To a stirred suspension of Fmoc-lysine (368 mg, 1.0 mmol) in EtOH (3 mL) was added dropwise at 0° C. a 5% (w/v) aqueous solution of $Na_2CO_3$ (3 mL). Methyl dithiomyristate (1.1 mmol) was then added dropwise at 0° C. After the addition was complete, the reaction mixture was stirred at room temperature overnight before the addition of a 50% (v/v)

solution of EtOH in double deionized water (3 mL). Ethanol was removed under reduced pressure and the residual aqueous solution was acidified with 6N HCl to pH 1-2 and extracted with dichloromethane. The combined organic layer was washed with brine, dried over anhydrous $Na_2SO_4$, filtered, and concentrated under reduced pressure, affording an oily residue from which the product was isolated via silica gel column chromatography as a light yellow solid (307 mg, 52%). LCMS (ESI) calcd. for $C_{35}H_{50}N_2O_4S$ [M+H]$^+$ 595.4, obsd. 595.3.

Thiomyristoyl peptide was synthesized on Fmoc-Wang resin using standard Fmoc/tBu chemistry O-benzotriazol-N,N,N',N'-tetramethyluronium hexafluorophosphate/1-hydroxybenzotriazol (HBTU/HOBt) protocol. Modified lysine was incorporated using Fmoc-Lys(thiomyristoyl)-OH. Cleavage from the resin and removal of all protecting groups were done by incubating the resin with trifluoroacetic acid (TFA) containing phenol (5%), thioanisole (5%), ethanedithiol (2.5%), and water (5%) for 2 hours. The crude peptide was purified by reverse phase HPLC on BECKMAN COULTER System Gold 125P solvent module & 168 Detector with a TARGA C18 column (250×20 mm, 10 μm, Higgins Analytical, Inc., Mountain View, Calif.) monitoring at 215 nm. Mobile phases used were 0.1% aqueous TFA (solvent A) and 0.1% TFA in acetonitrile (solvent B). Peptide was eluted with a flow rate of 10 mL/min with the following gradient: 0% solvent B for 5 min, then 0% to 25% solvent B over 25 min. The identity and purity of the peptides were verified by LCMS. ARK(thiomyristoyl)ST peptide, LCMS (ESI) calcd. for $C_{36}H_{69}N_9O_8S$ [M+H]$^+$ 788.5, obsd. 788.2.

Elucidation of the Deacylase Activity of Sirt6 and PfSir2a

Several H3 K9 peptides with different acyl groups on Lys9 were synthesized. These peptides include biotinyl, lipoyl, malonyl, succinyl, 3-hydroxy-3-methylglutaryl, myristoyl, and palmitoyl groups. Initial testing using recombinant Sirt6 showed that both myristoyl and palmitoyl can be hydrolyzed by Sirt6. Monitoring the time course of the Sirt6-catalyzed deacetylation and demyristoylation reactions using the H3 K9 peptides revealed that demyristoylation is faster than deacetylation (data not shown). This is further confirmed by kinetic measurements, as shown in Table 1 below. With the same H3K9 peptide sequence, the $k_{cat}/K_m$ value of demyristoylation is 185 ($k_{cat}$=0.0078 s$^{-1}$, $K_m$=43 μM), which is more than 30-fold better than that of deacetylation ($k_{cat}/K_m$= 5.3 s$^{-1}$M$^{-1}$).

TABLE 1

Kinetic parameters of Sirt6 on H3 K9 acetyl and myristoyl peptides.

| | | $k_{cat}$ (s$^{-1}$) | $K_m$ for peptide (μM) | $k_{cat}/K_m$ (s$^{-1}$M$^{-1}$) |
|---|---|---|---|---|
| Sirt1 | deacetylation | 0.039 ± 0.001 | 38 ± 4 | 1.0 × 10$^3$ |
| Sirt6 | deacetylation | 0.0023 ± 0.0004 | 430 ± 150 | 5.3 |
| | demyristoylation | 0.0078 ± 0.0003 | 43 ± 7 | 1.8 × 10$^2$ |
| PfSir2a | deacetylation | 0.001 ± 0.0002 | 39 ± 9 | 26 |
| | demyristoylation | 0.01 ± 0.002 | <1.0* | >1.0 × 10$^4$ |

*The $K_m$ value cannot be accurately determined due to the detection limit when substrate concentration was lower than 1 μM.

Figure 1B:
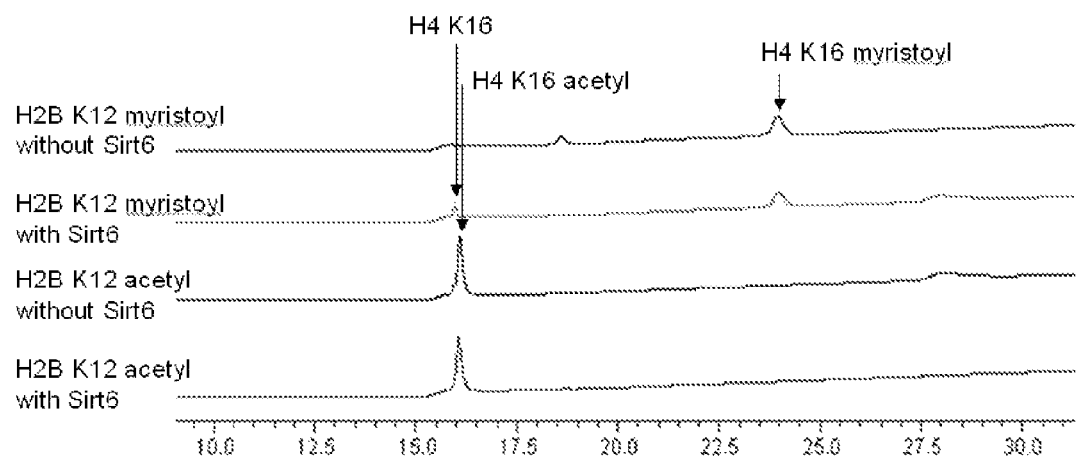

The deacetylase activity of Sirt6 has been reported to be sequence-specific. Thus far, only H3 K9 and H3 K56 acetyl peptides have been reported to be the substrates of Sirt6. This is in contrast to what was reported for sirtuins with good deacetylase activity, such as Sirt1 and yeast HST2, which can deacetylate acetyl lysine in many different peptide sequences. Now that a more efficient activity has herein been found for Sirt6, a further study was conducted to determine whether the more efficient demyristoylation activity also allows Sirt6 to accept more peptide sequences as substrates. For this purpose, acetyl and myristoyl peptides were synthesized based on the H2B K12, and H4 K16 sequences. Significantly, the hydrolysis of the acetyl peptides by Sirt6 was essentially undetectable based on HPLC analysis, as shown in the HPLC traces comparing H2B K12 acetyl with H2B K12 myristoyl (FIG. 1A) and HPLC traces comparing H4 K16 acetyl with H4 K16 myristoyl (FIG. 1B). In contrast, the hydrolysis of the corresponding myristoyl peptides can be readily detected, as further demonstrated by the HPLC traces shown in FIG. 1A and FIG. 1B. These results further support the idea that the demyristoylase activity of Sirt6 is significantly higher than its deacetylase activity. Thus, by using a suitable acyl group, Sirt6 can catalyze the hydrolysis of acyl lysine on a variety of different peptide sequences.

Figure 2:
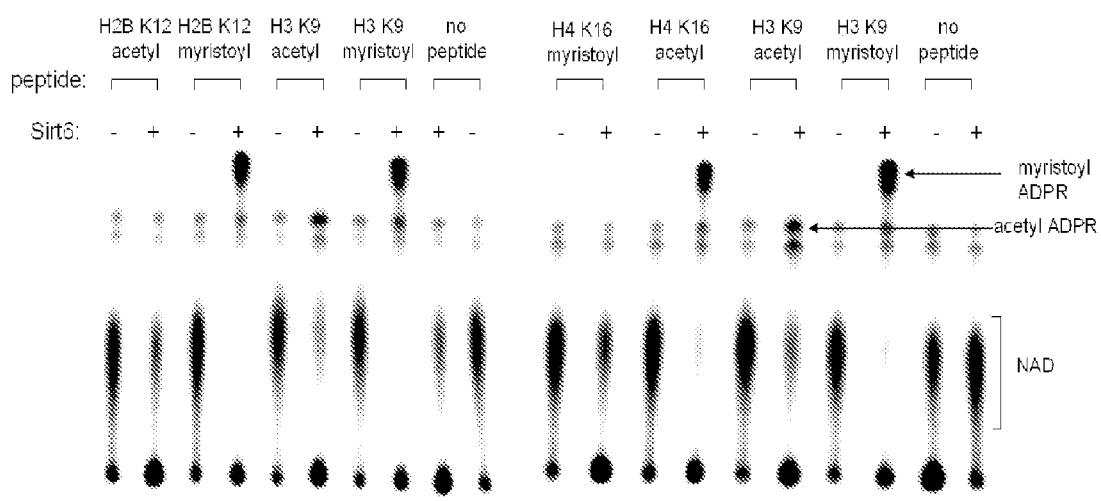
FIG. 2. $^{32}$P-NAD autoradiographic assay results of different peptides (20 μM) incubated with Sirt6 (1 μM) and $^{32}$P-NAD (0.1 μCi) at 37° C. for 2 hours. The reactions were resolved by thin-layer chromatography (TLC) plate and the $^{32}$P-labeled NAD end products were detected by autoradiography. Sirt6-catalyzed demyristoylation was detected with all myristoyl peptides, but Sirt6-catalyzed deacetylation was only detected with the H3 K9 acetyl peptide. Hydrolysis of myristoyl peptides is more efficient than acetyl peptides based on the $^{32}$P-NAD assay.

To further confirm the result, a $^{32}$P-NAD-based biochemical assay was also conducted. Based on the known deacetylation mechanism of sirtuins, the demyristoylation by Sirt6 should generate 2'-O-myristoyl ADP-ribose. When incubating myristoyl H3K9 with Sirt6 and $^{32}$P-NAD, most NAD was consumed and a new spot that runs almost at the solvent front was observed (FIG. 2). This is consistent with the formation of 2'-O-myristoyl ADP-ribose, since the hydrophobic myristoyl will make the compound less polar. When acetyl H3K9 peptide was incubated with Sirt6 and $^{32}$P-NAD, although a new product (2'-O-acetyl ADPR) spot was observed, there were still NAD molecules left (FIG. 2), suggesting that Sirt6 demyrisotylation is more efficient than deacetylation. With the H2B K12 and H4 K16 peptides, demyristoylation was observed but deacetylation was not observed in the $^{32}$P-NAD assay with Sirt6 (FIG. 2). Therefore, the $^{32}$P-NAD assay results are consistent with the HPLC assay described above and suggest that Sirt6 has robust demyristoylase activity.

Figure 3:
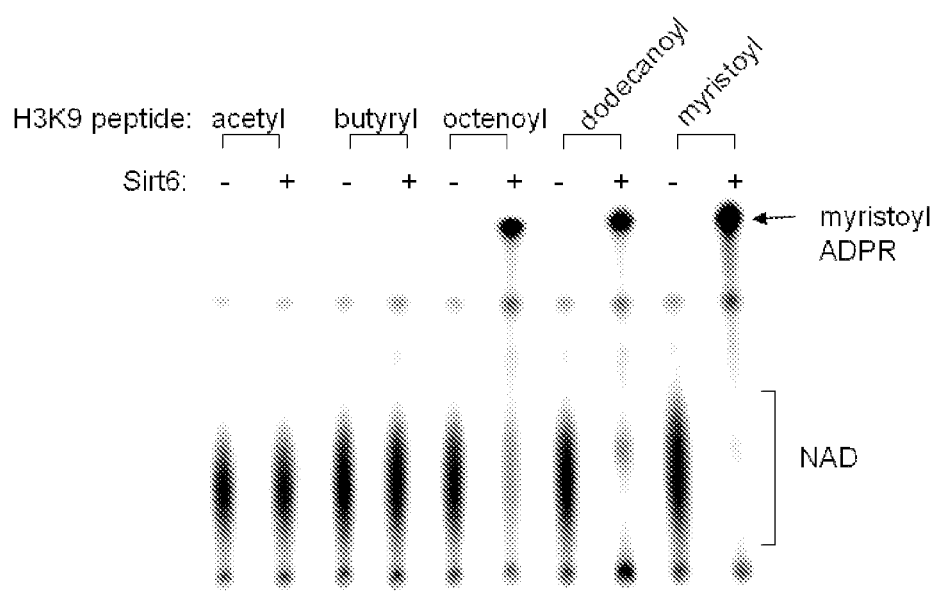
FIG. 3. $^{32}$P-NAD assay results of different peptides in accordance with the procedure used in FIG. 2, except that acetyl, octenoyl, dodecanoyl, and myristoyl groups are compared in H3K9 peptide. As shown, the longer acyl groups (octenoyl, dodecanoyl, and myristoyl) can be hydrolyzed more efficiently by Sirt6.

In addition to acetyl and myristoyl, butyryl, octenoyl, and dodecanoyl peptides were also studied in the $^{32}$P-NAD assay. Among these different acyl groups, the longer acyl chains appear to be hydrolyzed more efficiently than the shorter acyl chains (FIG. 3). Octenoyl, dodecanoyl, and myristoyl peptides can all be hydrolyzed by Sirt6 with the consumption of most of the $^{32}$P-NAD molecules. These results suggest that Sirt6 prefers longer fatty acyl groups on lysine peptides as substrates.

*Plasmodium falciparum* Sir2a (PfSir2a) is also known to remove modifications on histones. The instant data confirm that similar to Sirt6, PfSir2a's deacetylase activity is much lower compared with that of Sirt1 (Table 1). Using the H3 K9 peptides with different acyl groups, it has herein been found that PfSir2a also can remove fatty acyl group from peptides very efficiently. The demyristoylase activity of PfSir2a is greater than 300-fold better than its deacetylase activity (Table 1).

Histone Fatty Acylation as Novel Epigenetic Modifications

Figure 4A:
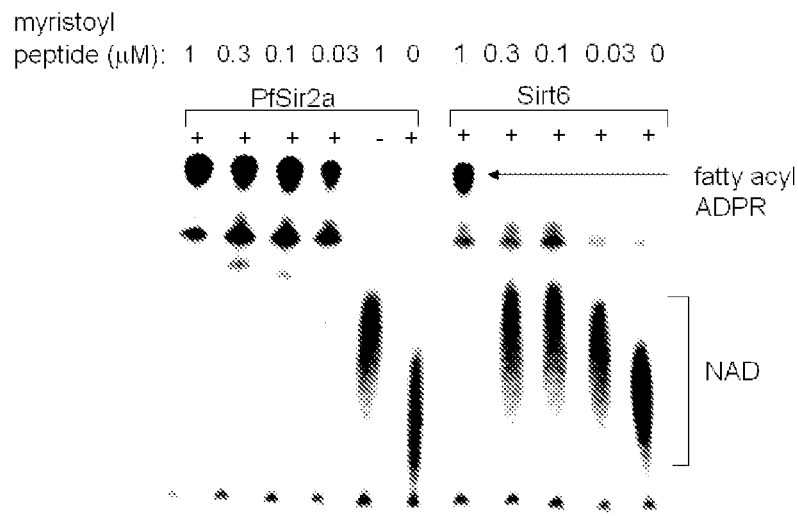
FIGS. 4A, 4B. (A) $^{32}$P-NAD assay results of H3K9 myristoyl peptide with Sirt6 and PfSir2a showing that PfSir2a has a lower detection limit of myristoyl peptides and can detect the demyristoylation of as low as 0.03 μM of myristoyl peptides. (B) $^{32}$P-NAD assay results of H3K9 myristoyl peptide when calf thymus histones were incubated with PfSir2a and $^{32}$P-NAD, showing the formation of the fatty acyl ADPR spot (as detected), which supports the concept that histones have fatty acyl lysine modification.
Figure 4B:
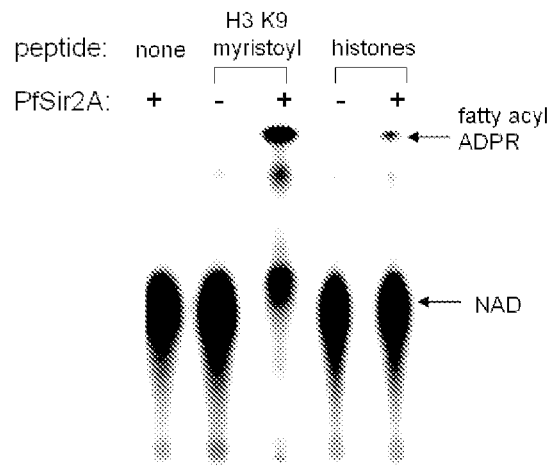

Protein lysine fatty acylation, although not commonly known, is known to occur for a few proteins. The fact that Sirt6 can efficiently remove fatty acyl groups from lysine residues suggests that lysine fatty acylation could be more common than previously thought. Because Sirt6 was thought to remove modifications on histones, a study was conducted to find out whether histones have fatty acyl modifications. Specifically, a study was conducted to explore whether Sirt6 or PfSir2a and $^{32}$P-NAD can be used to detect the presence of fatty acyl lysine residues on histones. In the study, the detection limit of PfSir2a and Sirt6 was tested using synthetic H3 K9 myristoyl peptide. As shown in FIG. 4A, the demyristoylation of as low as 0.03 µM of myristoyl peptide can be detected with PfSir2a under the conditions used. In contrast, with Sirt6, the demyristoylation reaction cannot be detected when 0.3 µM or lower concentrations of myristoyl peptide is present. Thus, under the conditions used, PfSir2a can be used to detect lower levels of fatty acyl lysine peptides. For this reason, in later studies, PfSir2a was used to detect the presence of fatty acyl lysine in histones. Commercial calf thymus histones were incubated with $^{32}$P-NAD and PfSir2a, and the formation of O-fatty acyl ADPR was detected (FIG. 4B), suggesting that fatty acylation of lysine residues does occur on histones.

The above data suggest that both human Sirt6 and PfSir2a, which have weak deacetylase activities, can catalyze the hydrolysis of long fatty acyl lysine modifications much more efficiently. Furthermore, lysine fatty acylation was found to occur on calf thymus histones. The combination of the enzymology data and the presence of fatty acyl lysines on histones suggest that removing the long fatty acyl chains from histones should be the physiological functions of Sirt6 and PfSir2a. These findings sharply contrast with the idea prevalent in the art that both Sirt6 and PfSir2a were thought to regulate transcription of certain genes by removing acetyl lysine modifications on histones. The data herein suggest that longer fatty acyl lysine modifications are also involved in transcriptional regulation.

Figures 6A, 6B:
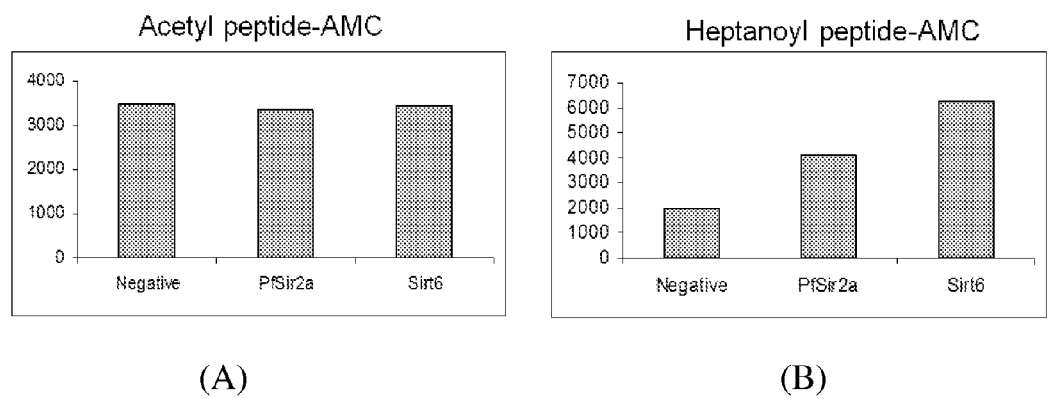
FIGS. 6A, 6B. Charts showing the difference between fluorogenic acetyl peptide-AMC substrate (A) and heptyl peptide-AMC substrate (B) detection ability of Sirt6 and PfSir2 activity. As shown, whereas the heptyl peptide-AMC was found to be highly effective for detecting Sirt6 and PfSir2 activity, the acetyl peptide-AMC was found to be ineffective for this purpose.

Development of Sirt6 and PfSir2a Activity Assays for Screening of Candidate Compounds For sirtuins with robust deacetylase activity, a fluorogenic assay has been used to detect the activity and screen for inhibitors/activators (FIG. 5, top). This assay uses an acetyl peptide with an aminocoumarin (AMC) molecule attached to the carboxylate of the acetyl lysine residue. After a sirtuin removes the acetyl group, the AMC can be released by trysin, which produces a fluorescence signal. Thus, the presence of a compound that can change the activity of sirtuin being analyzed can be detected by monitoring the fluorescence released in the reaction. However, with an acetyl peptide (e.g., ISGASEAcK) conjugated to AMC, the activity of Sirt6 or PfSir2 was not detectable, as shown by comparing FIGS. 6A and 6B. This finding is consistent with the weak deacetylase activity of these two sirtuins, as shown in Table 1. Based on the finding that Sirt6 and PfSir2a prefer longer fatty acyl groups on lysine residues, a heptanoyl peptide-AMC compound (FIG. 5, bottom) was prepared and studied. As shown by FIG. 6B, the heptanoyl peptide-AMC compound can be used to detect the activity of Sirt6 and PfSir2a, whereas such utility is not found in acetyl peptide-AMC. The system can be further optimized by trying different peptide sequences and different acyl groups.

The Development of Sirt6 and PfSir2a Inhibitors

Figure 7A:
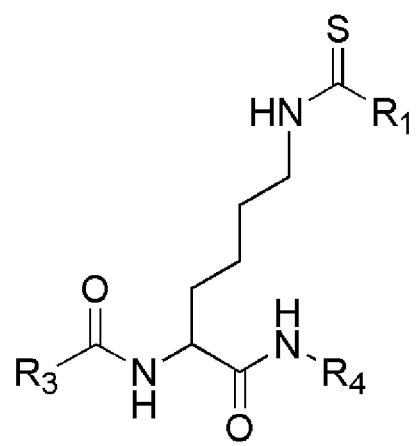
FIGS. 7A, 7B. Chemical structures of a generic subset of thioamide compounds within Formula 1a (top, FIG. 7A), and a specific thioamide compound (bottom, FIG. 7B) within the generic subset.
Figure 7B:
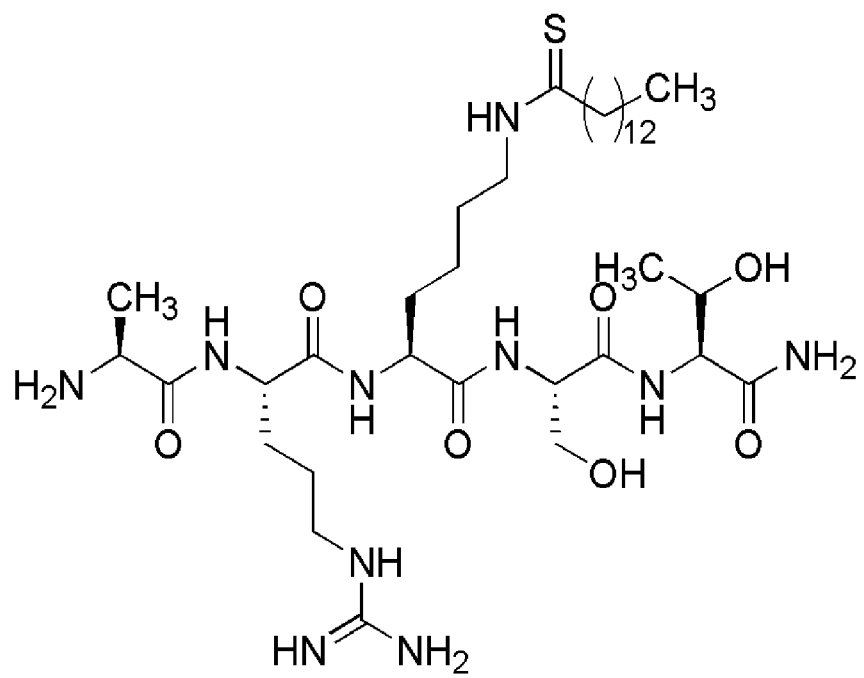

Based on the finding that Sirt6 and PfSir2a prefer longer fatty acyl groups on lysine residues, an exemplary generic inhibitor structure was herein designed for Sirt6 and PfSir2a, as depicted in FIG. 7A, wherein each of the generic groups (e.g., $R_1$, $R_3$, and $R_4$) retain their meanings, as defined above. In the structure shown in FIG. 7A, $R_1$, $R_3$, and $R_4$ and other aspects of the structure can be systematically varied to increase the potency and other desired properties of the compound. The $R_1$ group is preferably a large hydrophobic group based on the fact that long fatty acyl chains are preferred. One particular compound (FIG. 7B) has been prepared and shown to inhibit Sirt6 and PfSir2a with 50% inhibition concentration of 5 and 30 mM, respectively. Thus, the general inhibitor structure design is valid and it should be feasible to further improve the potency of the inhibitor by varying $R_1$, $R_3$, and $R_4$.

While there have been shown and described what are at present considered the preferred embodiments of the invention, those skilled in the art may make various changes and modifications which remain within the scope of the invention defined by the appended claims.

What is claimed is:

1. A compound that modulates Sirt6, PfSir2a, or Sirt7 deacylase activity, having the following chemical structure:

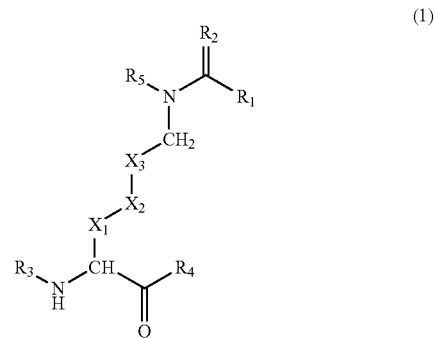

(1)

wherein $R_1$ is a hydrocarbon group having at least five carbon atoms connected by carbon-carbon bonds, wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or $NH_2$ group, and wherein one or more hydrogen atoms in said hydrocarbon group is optionally replaced with fluoro atoms;

$R_2$ is selected from S, $NR_6$, and 0, wherein $R_6$ is a hydrogen atom or a hydrocarbon group R;

$X_1$, $X_2$, and $X_3$ are each —$(CH_2)_n$—, wherein n independently represents 1, 2, or 3;

$R_5$ is a hydrogen atom or a hydrocarbon group R;

$R_3$ and $R_4$ are independently hydrogen atom or a hydrocarbon group R;

wherein said hydrocarbon groups R are independently either unsubstituted or substituted with one or more heteroatoms selected from N, O, S, P, and F or heteroatom groups containing one or more of said heteroatoms, wherein $R_4$ can alternatively be OH or SH.

2. The compound of claim 1, wherein said hydrocarbon group for $R_1$ has at least five carbon atoms connected by carbon-carbon bonds in the absence of heteroatom substitution, except that one or more hydrogen atoms are optionally replaced with fluoro atoms.

3. The compound of claim 1, wherein said hydrocarbon group for $R_1$ has at least six carbon atoms connected by carbon-carbon bonds wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or $NH_2$ group, and wherein one or more hydrogen atoms in said hydrocarbon group is optionally replaced with fluoro atoms.

4. The compound of claim 1, wherein said hydrocarbon group for $R_1$ has at least seven carbon atoms connected by carbon-carbon bonds wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or NH$_2$ group, and wherein one or more hydrogen atoms in said hydrocarbon group is optionally replaced with fluoro atoms.

5. The compound of claim 1, wherein said hydrocarbon group for R$_1$ has at least eight carbon atoms connected by carbon-carbon bonds wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or NH$_2$ group, and wherein one or more hydrogen atoms in said hydrocarbon group is optionally replaced with fluoro atoms.

6. The compound of claim 1, wherein said hydrocarbon group for R$_1$ has up to twenty carbon atoms.

7. The compound of claim 1, wherein R$_2$ is S.

8. The compound of claim 1, wherein R$_3$ and R$_4$ are each comprised of at least one amino acid residue.

9. A compound that functions as an acylated substrate in an assay for Sirt6, PfSir2a, or Sirt7 deacylase activity, having the following chemical structure:

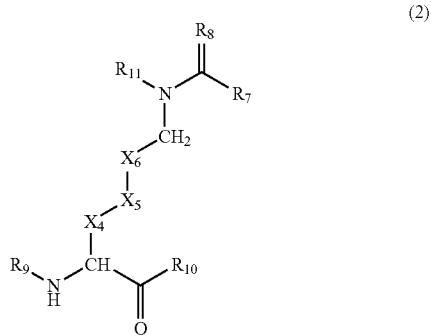

(2)

wherein R$_7$ is a hydrocarbon group having at least five carbon atoms connected by carbon-carbon bonds, wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or NH$_2$ group, and wherein one or more hydrogen atoms in said hydrocarbon group is optionally replaced with fluoro atoms;

R$_8$ is selected from S, NR$_{13}$, and O, wherein R$_{13}$ is a hydrogen atom or a hydrocarbon group R;

X4, X5, and X6 are each —(CH2)n-, wherein n independently represents 1, 2, or 3;

R$_{11}$ is a hydrogen atom or a hydrocarbon group R;

R$_9$ and R$_{10}$ are independently hydrogen atom or a hydrocarbon group R, wherein R$_{10}$ can alternatively be OH or SH, and wherein at least one of R$_9$ and R$_{10}$ is an indicator moiety;

wherein said hydrocarbon groups R are independently either unsubstituted or substituted with one or more heteroatoms selected from N, O, S, P, and F or heteroatom groups containing one or more of said heteroatoms.

10. The compound of claim 9, wherein said indicator moiety is a fluorophore.

11. The compound of claim 10, wherein said fluorophore has an aminocoumarin structure.

12. The compound of claim 9, wherein said hydrocarbon group for R$_7$ has at least five carbon atoms connected by carbon-carbon bonds in the absence of heteroatom substitution, except that one or more hydrogen atoms are optionally replaced with fluoro atoms.

13. The compound of claim 9, wherein said hydrocarbon group for R$_7$ has at least six carbon atoms connected by carbon-carbon bonds wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or NH$_2$ group, and wherein one or more hydrogen atoms in said hydrocarbon group is optionally replaced with fluoro atoms.

14. The compound of claim 9, wherein said hydrocarbon group for R$_7$ has at least seven carbon atoms connected by carbon-carbon bonds wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or NH$_2$ group, and wherein one or more hydrogen atoms in said hydrocarbon group is optionally replaced with fluoro atoms.

15. The compound of claim 9, wherein said hydrocarbon group for R$_7$ has at least eight carbon atoms connected by carbon-carbon bonds wherein said hydrocarbon group optionally includes one heteroatom selected from O, N, and S that interrupts a carbon-carbon bond of said hydrocarbon group or replaces a carbon atom of said hydrocarbon group, except that said heteroatom is not included as an OH, SH, or NH$_2$ group, and wherein one or more hydrogen atoms in said hydrocarbon group is optionally replaced with fluoro atoms.

16. The compound of claim 9, wherein said hydrocarbon group for R$_7$ has up to twenty carbon atoms.

17. The compound of claim 9, wherein R$_8$ is S.

18. The compound of claim 9, wherein one of R$_9$ and R$_{10}$ is comprised of at least one amino acid residue, and one of R$_9$ and R$_{10}$ is an indicator moiety.

19. The compound of claim 9, wherein said indicator moiety is a fluorophore.

20. The compound of claim 19, wherein said fluorophore has an aminocoumarin structure.

21. A method for treating a subject afflicted with a disorder characterized by an abnormal or non-optimal Sirt6 or Sirt7 deacylase activity, comprising administering to said subject a compound of claim 1 in a pharmaceutically effective amount for treating said disorder.

* * * * *